US010726957B2

(12) United States Patent
D'Amelia

(10) Patent No.: US 10,726,957 B2
(45) Date of Patent: Jul. 28, 2020

(54) SYSTEMS AND METHODS FOR PREDICTING AND DETECTING HAZARDOUS CONDITIONS AND FACILITATING REGULATORY COMPLIANCE THROUGH AUTOMATED COMMUNICATION PLATFORMS

(71) Applicant: Philip Thomas D'Amelia, Nesconset, NY (US)

(72) Inventor: Philip Thomas D'Amelia, Nesconset, NY (US)

(73) Assignee: VITRALOGY IP, LLC, Bohemia, NY (US)

(*) Notice: Subject to any disclaimer, the term of this patent is extended or adjusted under 35 U.S.C. 154(b) by 312 days.

(21) Appl. No.: 15/715,698

(22) Filed: Sep. 26, 2017

(65) Prior Publication Data
US 2019/0027255 A1  Jan. 24, 2019

Related U.S. Application Data

(60) Provisional application No. 62/399,963, filed on Sep. 26, 2016.

(51) Int. Cl.
| | |
|---|---|
| *G16H 50/80* | (2018.01) |
| *H04Q 9/00* | (2006.01) |
| *G16H 40/20* | (2018.01) |
| *G08B 21/12* | (2006.01) |
| *G08B 31/00* | (2006.01) |
| *G16H 40/63* | (2018.01) |
| *G16H 40/67* | (2018.01) |

(Continued)

(52) U.S. Cl.
CPC ....... *G16H 50/80* (2018.01); *G06Q 10/06311* (2013.01); *G08B 21/12* (2013.01); *G08B 31/00* (2013.01); *G16H 40/20* (2018.01); *G16H 40/63* (2018.01); *G16H 40/67* (2018.01); *H04Q 9/00* (2013.01); *G08B 27/006* (2013.01); *H04Q 2209/823* (2013.01)

(58) Field of Classification Search
None
See application file for complete search history.

(56) References Cited

U.S. PATENT DOCUMENTS

| | | | | |
|---|---|---|---|---|
| 5,236,600 A | * | 8/1993 | Hutchins | A61L 2/18 210/739 |
| 10,126,284 B1 | * | 11/2018 | Jenkins | G01N 33/18 |

(Continued)

FOREIGN PATENT DOCUMENTS

WO  WO-2014026168 A1 * 2/2014  ............. G16H 40/20

*Primary Examiner* — Michael Tomaszewski
*Assistant Examiner* — Jay M. Patel
(74) *Attorney, Agent, or Firm* — Bryan Cave Leighton Paisner, LLP

(57) ABSTRACT

This disclosure relates to an automated and comprehensive communications and monitoring platform that enables conditions to be monitored at one or more sites, and which includes a set of tools for preventing, mitigating and/or remediating occurrences of unfavorable conditions, such as hazardous biological/chemical conditions or device failures at the sites. Historical data aggregated by the platform is utilized to predict occurrences of hazardous or unfavorable conditions. Automated remediation actions are triggered to cure or prevent the occurrences of the hazardous or unfavorable conditions.

21 Claims, 12 Drawing Sheets

(51) Int. Cl.
*G08B 27/00* (2006.01)
*G06Q 10/06* (2012.01)

(56) References Cited

U.S. PATENT DOCUMENTS

| | | | | |
|---|---|---|---|---|
| 2005/0080520 | A1* | 4/2005 | Kline | B03B 9/06 |
| | | | | 701/1 |
| 2005/0089441 | A1* | 4/2005 | Coffey | F28F 25/00 |
| | | | | 422/1 |
| 2006/0218010 | A1* | 9/2006 | Michon | G06F 19/3456 |
| | | | | 705/3 |
| 2007/0090059 | A1* | 4/2007 | Plummer | E03B 7/02 |
| | | | | 210/743 |
| 2008/0162088 | A1* | 7/2008 | DeVaul | A61B 5/0024 |
| | | | | 702/190 |
| 2008/0280299 | A1* | 11/2008 | Calvo | C12Q 1/689 |
| | | | | 435/6.12 |
| 2009/0125460 | A1* | 5/2009 | Hewison | G06N 3/004 |
| | | | | 706/11 |
| 2010/0144383 | A1* | 6/2010 | Berger | G06Q 10/06 |
| | | | | 455/521 |
| 2013/0110580 | A1* | 5/2013 | Sholl | G06Q 30/018 |
| | | | | 705/7.28 |
| 2014/0046722 | A1* | 2/2014 | Rosenbloom | G06Q 10/06 |
| | | | | 705/7.28 |
| 2014/0154789 | A1* | 6/2014 | Polwart | G01N 33/56911 |
| | | | | 435/287.2 |
| 2014/0222522 | A1* | 8/2014 | Chait | G06Q 10/0637 |
| | | | | 705/7.36 |
| 2015/0100345 | A1* | 4/2015 | Holmes | G16H 50/80 |
| | | | | 705/2 |
| 2016/0122831 | A1* | 5/2016 | West | C12Q 1/6886 |
| | | | | 514/49 |
| 2017/0218455 | A1* | 8/2017 | Steelman | C12Q 1/6806 |
| 2018/0052970 | A1* | 2/2018 | Boss | G16H 50/30 |
| 2019/0079064 | A1* | 3/2019 | Jenkins | G01N 33/18 |

* cited by examiner

300B

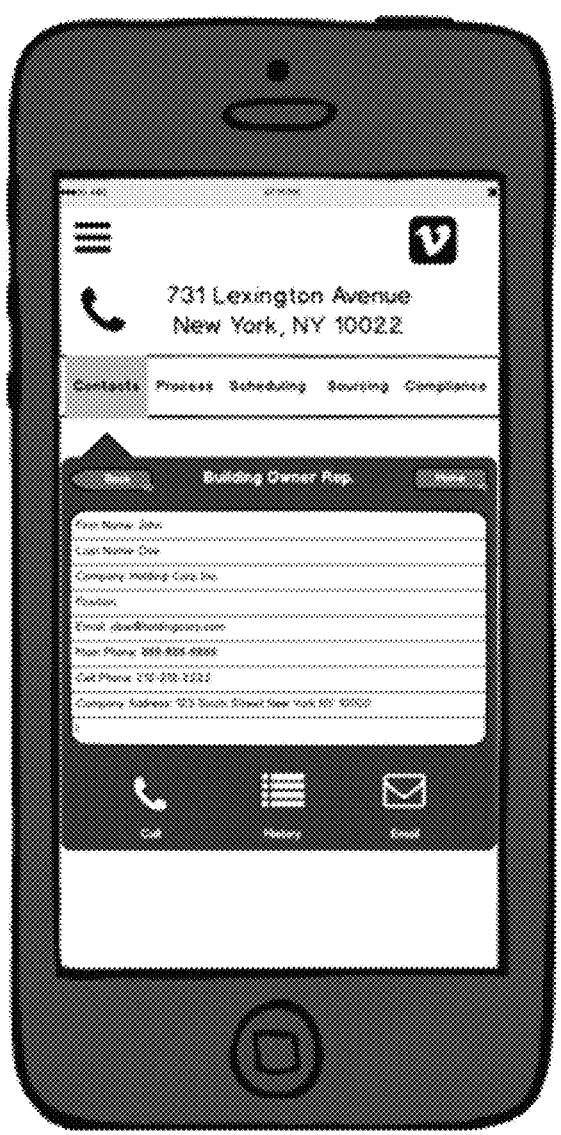
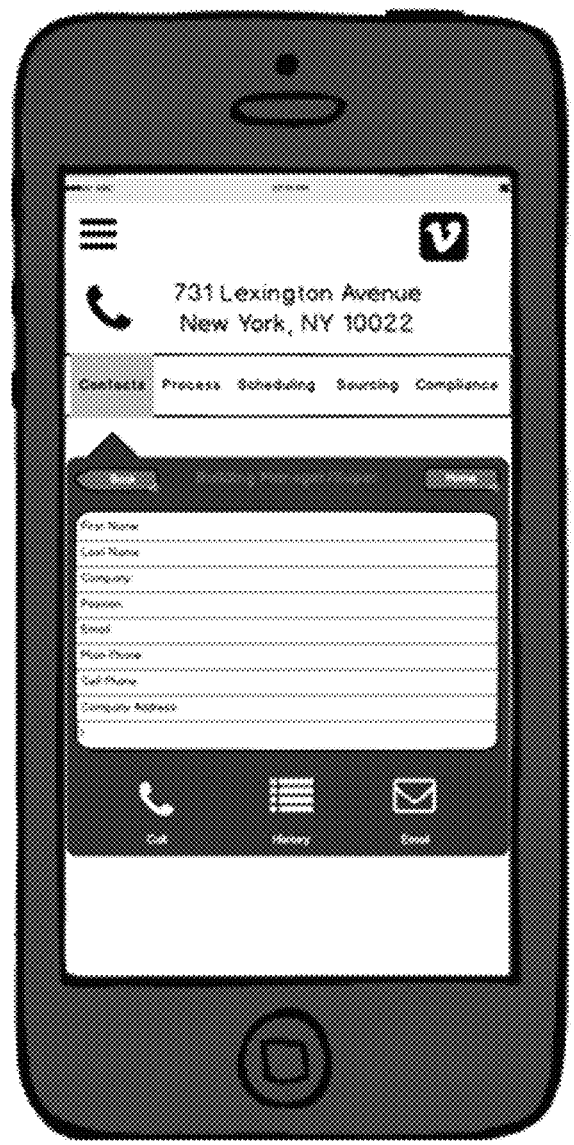
Figure 3C
Figure 3D

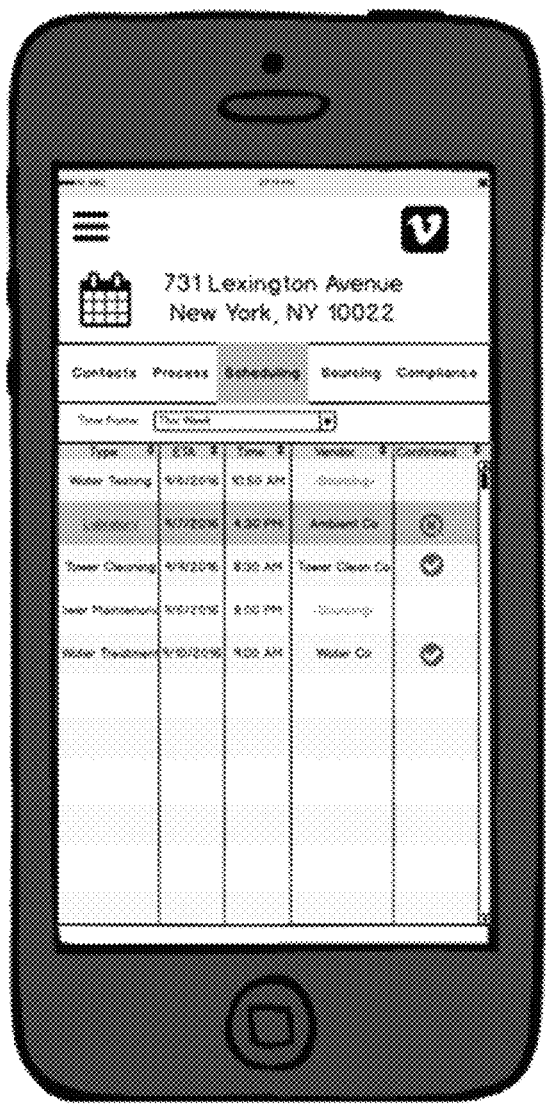
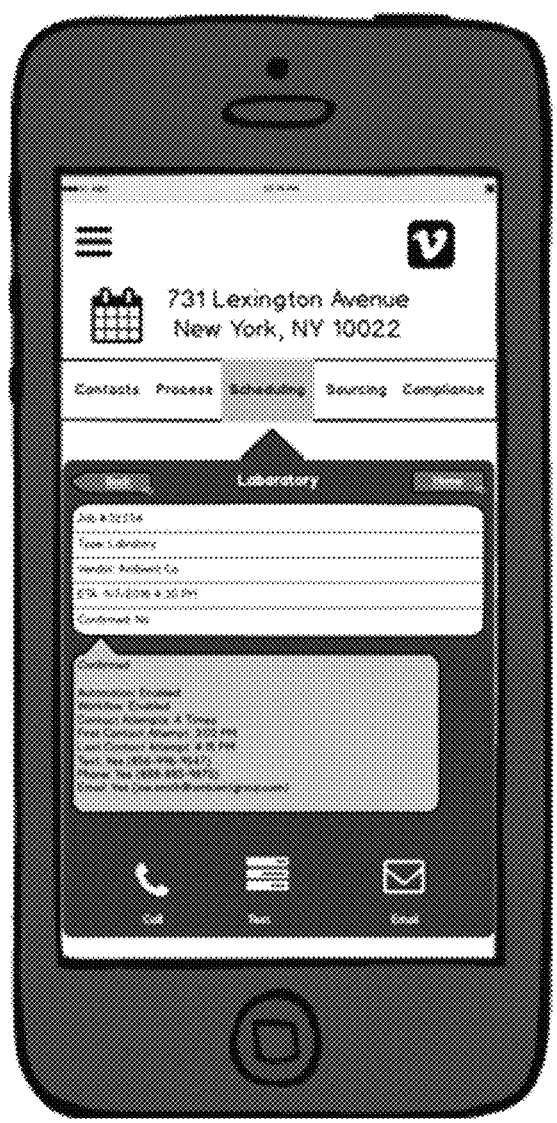
Figure 3G
Figure 3H

300I 300J
300K
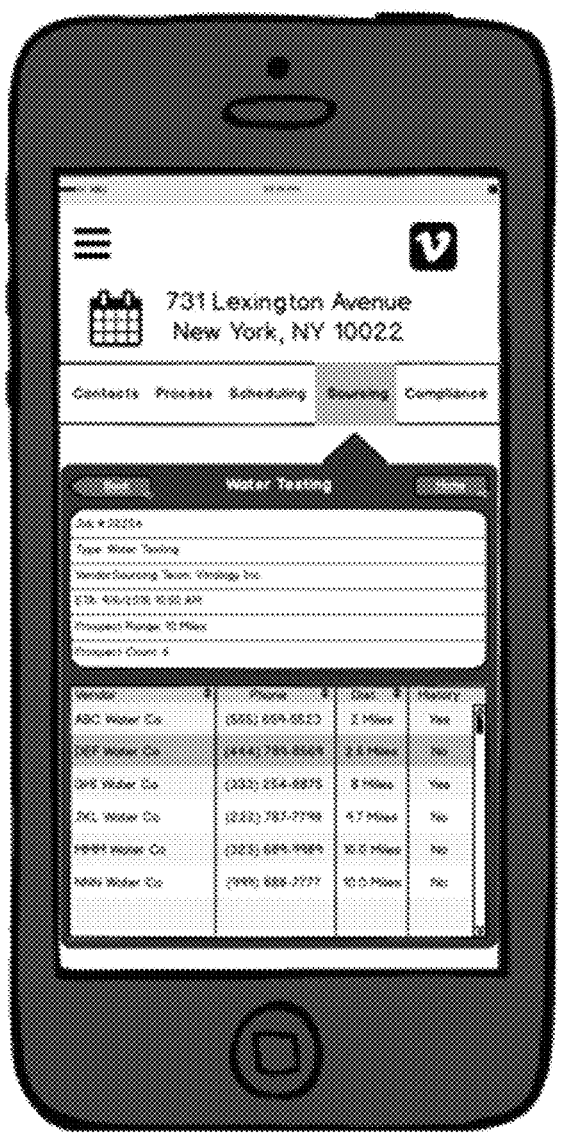
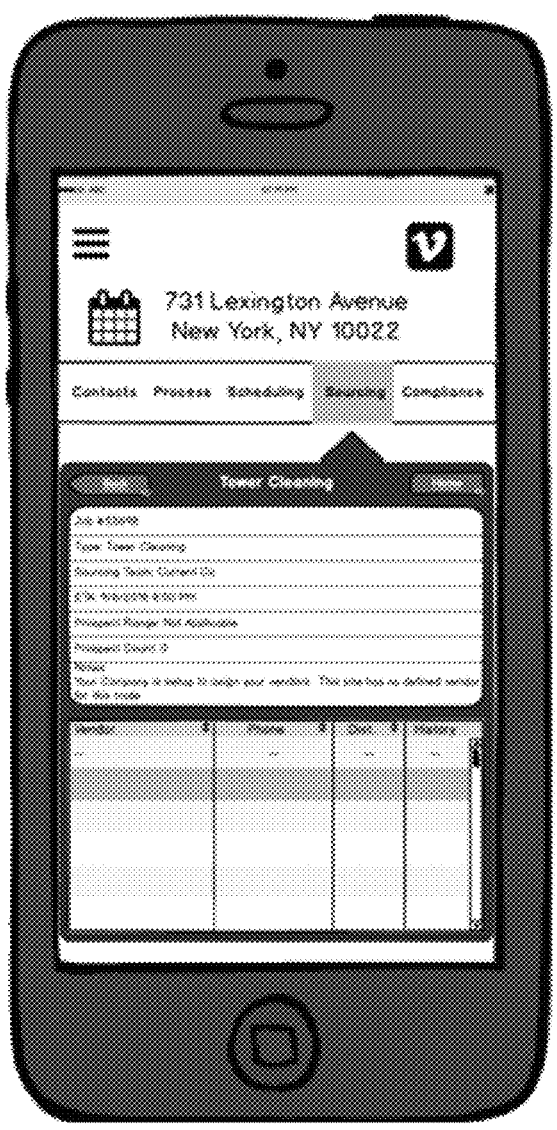
Figure 3J
Figure 3K

SYSTEMS AND METHODS FOR PREDICTING AND DETECTING HAZARDOUS CONDITIONS AND FACILITATING REGULATORY COMPLIANCE THROUGH AUTOMATED COMMUNICATION PLATFORMS

CROSS-REFERENCE TO RELATED APPLICATIONS

The present application claims the benefit of U.S. Provisional Application No. 62/399,963 filed on Sep. 26, 2016, the content of which is herein incorporated by reference in its entirety.

TECHNICAL FIELD

The present disclosure is directed to a communications platform that automates the management of tasks and services at one or more sites and ensures compliance with corresponding regulatory requirements and, more particularly, to a platform that is configured to monitor environmental or other conditions across multiple sites or facilities, manage associated tasks and services, and interconnect users and service providers to manage the implementation and ensure completion of such tasks and services in an efficient and compliant fashion.

BACKGROUND

Property managers are typically responsible for managing sites (e.g., residential buildings, commercial buildings, industrial buildings, facilities or types of property locations) and monitoring various conditions at these sites. Monitoring and managing multiple sites can be labor-intensive and requires high levels of attention to be devoted to scheduling vendors to perform various tasks. Such activities are particularly challenging in view of complex regulatory climates which require the property managers to undertake various actions to ensure compliance with applicable regulations and laws (e.g., such as environmental regulations which may require compliance with applicable state, federal and local environmental regulations and laws). In addition to understanding and keeping up with the current obligations that are imposed by these regulations, property owners are faced with the daunting task of coordinating and scheduling activities among multiple vendors and other parties to perform tasks in connection with compliance measures. The coordinating and scheduling activities are resource-intensive and prone to significant errors when performed manually or by persons. Such errors can be particularly costly in terms of fines that may be imposed and/or revocations of licenses.

For example, the New York City Department of Health and Mental Hygiene has recently enacted environmental regulations which pertain to treating water stored in water or cooling towers for legionella and other biological agents. In order to comply with these regulations, property managers are required to undertake different types of tasks (e.g., such as submitting water samples for laboratory testing, cleaning and treating water with biocides, cleaning water tower structures, draining and filling the tower structures, and performing maintenance on the tower structures and associated water systems). In addition to being complex, these tasks require coordination among many different parties (e.g., service providers for performing the tasks, individuals at the sites, and governmental compliance personnel). Moreover, many of these tasks are required to be completed within certain timeframes. The regulations impose very specific time limits for performing such tasks and failure to perform the tasks in the required timeframes can result in heavy fines.

In view of the foregoing, there is a need for a communications platform that can automate coordination and management of complex tasks and to ensure completion of compliance tasks within required timeframes.

SUMMARY

The inventive principles described herein relate to a communications and monitoring platform that automates actions for detecting hazardous conditions (e.g., biological/chemical hazards) and other unfavorable conditions (e.g., such as facility failures, disruptions or required maintenance), as well as for preventing, mitigating and/or remediating occurrences of the hazardous and unfavorable conditions. The platform provides automated tools for scheduling and managing tasks and services to be performed at the sites. In certain embodiments, equipment and sensors at the sites permit monitoring of the sites and permit remedial actions to be taken for preventing or curing conditions at the sites. The platform gathers all information associated with monitoring and managing the sites. The aggregated information is used to predict future occurrences of the hazardous or unfavorable conditions. Alerts are sent to appropriate individuals to take preventive actions prior to the occurrences of the predicted hazardous or unfavorable conditions.

According to certain embodiments, a system is provided for detecting hazardous biological conditions that includes: (a) a plurality of cooling or water tower structures located at a plurality of sites; (b) a database that stores historical data associated with monitoring biological conditions at the plurality of sites, the histological data at least including information associated with tracking legionella conditions in the cooling or water tower structures; and (c) at least one computing device having at least one processor and at least one physical storage device that stores instructions, wherein execution of the instructions by the at least one processor causes the at least one computing device to: provide an electronic platform that is configured to perform functions associated with monitoring and remediating biological conditions at the plurality of sites; receive monitoring information, via the electronic platform, from one or more of: sensory devices which provide real-time tracking of the biological conditions at the sites, and electronic devices that transmit the monitoring information over a network to track the biological conditions at the plurality sites; store the monitoring information in the database with the historical data; execute a prediction component which is configured to analyze the historical data and monitoring information to predict occurrences of hazardous legionella conditions at the plurality of sites; and generate an alert that provides information associated with the predicted occurrences of hazardous legionella conditions.

According to certain embodiments, a method is provided for detecting hazardous biological conditions, comprising: providing access to a database stored on a non-transitory storage device, the database including historical data associated with monitoring biological conditions at a plurality of sites, the histological data at least including information associated with tracking legionella conditions in cooling or water tower structures at the plurality of sites; providing access to an electronic platform that is configured to perform functions associated with monitoring and remediating biological conditions at the plurality of sites; receiving monitoring information, via the electronic platform, from one or more of: sensory devices which provide real-time tracking of the biological conditions at the sites, and electronic devices that transmit the monitoring information over a network to track the biological conditions at the plurality sites; storing the monitoring information in the database with the historical data; executing a prediction component which is configured to analyze the historical data and monitoring information to predict occurrences of hazardous legionella conditions at the plurality of sites; and generating an alert that provides information associated with the predicted occurrences of hazardous legionella conditions.

According to certain embodiments, a server is provided for detecting hazardous biological conditions, comprising: at least one computing device having at least one processor and at least one physical storage device that stores instructions, wherein execution of the instructions by the at least one processor causes the at least one computing device to: provide access to a database that includes historical data associated with monitoring biological, chemical or other hazardous conditions at a plurality of sites; provide access to an electronic platform that is configured to perform functions associated with monitoring and remediating hazardous conditions at the plurality of sites; receive monitoring information, via the electronic platform, from one or more of: sensory devices which provide real-time tracking of the hazardous conditions at the sites, and electronic devices that transmit the monitoring information over a network to track the hazardous conditions at the plurality of sites; store the monitoring information in the database; execute a prediction component which is configured to analyze the historical data and monitoring information to predict occurrences of hazardous conditions at the plurality of sites; and generate an alert that provides information associated with the predicted occurrences of hazardous conditions.

The foregoing and other features and advantages will become apparent from the following detailed description of illustrative embodiments thereof, which is to be read in connection with the accompanying drawings.

BRIEF DESCRIPTION OF DRAWINGS

The inventive principles are illustrated in the figures of the accompanying drawings which are meant to be exemplary and not limiting, in which like references are intended to refer to like or corresponding parts, and in which:

FIG. 3A is an illustration of an exemplary management interface displayed on a mobile device which provides an overview of compliance-related issues and scores for different sites;

FIG. 3C is an illustration of an exemplary contact details interface that provides contact information for a service provider;

FIG. 3D is an illustration of an exemplary contact details interface that provides a form for supplying information contact information for a service provider;

FIG. 3G is an illustration of an exemplary scheduling interface that displays information related to scheduling tasks;

FIG. 3H is an illustration of an exemplary scheduling details interface that displays additional details about the scheduling of the task;

FIG. 3J is an illustration of an exemplary sourcing details interface that includes a listing of prospective service providers for performing a selected task;

FIG. 3K is an illustration of an exemplary sourcing details interface that includes a form for adding service for performing a selected task;

FIG. 3N is an illustration of an exemplary scoring interface that illustrates how a compliance score compares to other scores;

DESCRIPTION OF EXEMPLARY EMBODIMENTS

Figure 1:
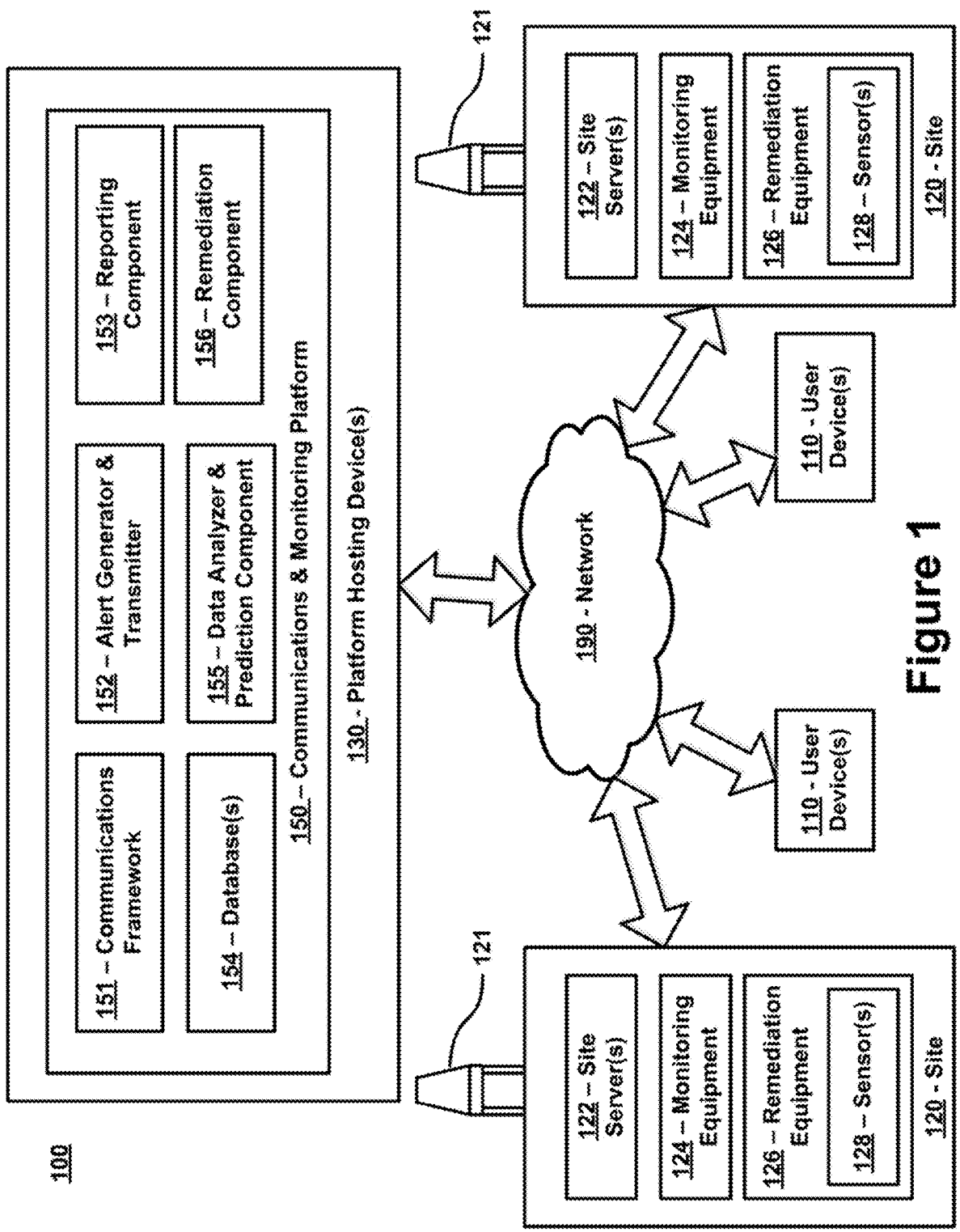
FIG. 1 is a block diagram of a system according to certain embodiments.

This disclosure relates to an automated and comprehensive communications and monitoring platform that enables conditions to be monitored at one or more sites and which includes a set of tools for preventing, mitigating and/or remediating occurrences of unfavorable conditions (e.g., hazardous biological/chemical conditions or device failures) at the sites. In certain embodiments, the platform is configured to monitor compliance with regulatory requirements at one or more sites, schedule and manage tasks and services to be performed at the sites, and establish a communications framework which interconnects and coordinates service providers for completing the tasks. The platform monitors relevant factors (e.g., environmental conditions) at the sites based on data supplied to the platform by service providers and/or data received from monitoring equipment located at the sites. The information aggregated by the platform is utilized to detect or predict unfavorable conditions at the sites, dispatch service providers for preventing or remediating the unfavorable conditions, and/or remotely activate remedial equipment to treat the unfavorable conditions. In certain embodiments, the platform is able to detect or predict unfavorable conditions by analyzing monitoring information in conjunction with historical data to identify patterns associated with the occurrences of the unfavorable conditions.

The platform's communications framework enables various stakeholders, including property owners, site or facilities managers, and/or service providers, to quickly and easily communicate, schedule tasks, and oversee the completion of such tasks to ensure compliance with the applicable regulations or for other reasons. Property managers can instantly and easily schedule certified service providers (also referred to herein as "vendors") to execute the tasks and supply information to the platform for verifying completion of the tasks. The platform automatically transmits alerts to property managers and/or service providers in response to detecting certain triggering events. For example, the platform sends alerts in response to determining that tasks should be scheduled to comply with the regulatory framework and/or in response to detecting unfavorable conditions (e.g., hazardous conditions, conditions which do not comply with regulations, conditions indicating rising levels of contamination, or otherwise undesirable conditions) at the sites that are not in compliance with the applicable regulations. Scores indicating compliance with applicable regulations at the sites are generated and dynamically updated for each site to assist property managers with identifying sites that require attention. An automated remediation component utilizes a set of stored rules to identify certain triggering events (e.g., receiving failed laboratory results or failing to schedule a compliance task) and to automatically take appropriate corrective measures for fulfilling compliance obligations.

The platform can be configured to assist property managers with fulfilling compliance obligations associated with any and all regulations, compliance obligations associated with any and all governmental regulations, and/or other duties associated with servicing or maintaining properties.

In one particularly useful application, the platform is configured to provide assistance with managing environmental conditions at the sites. For example, the platform provides assistance with fulfilling compliance obligations associated with environmental regulations related to cooling towers or water towers located at sites (e.g., such as the environmental regulations promulgated by the New York City Department of Health and Mental Hygiene in Title 24 of the Rules of the City of New York which pertain to treating water for legionella and other biological agents). The platform can additionally provide assistance managing environmental conditions and fulfilling compliance obligations with other types of environmental regulations, e.g., such those associated with air quality, soil quality, hazardous chemicals or substances (e.g., regulations associated with controlling asbestos, lead or radon levels), and biological substances (e.g., regulations associated with controlling mold, insects or rodents). The platform permits the property managers to schedule, manage, monitor and verify tasks associated with maintaining or remediating environmental conditions at the sites (e.g., tasks associated with cleaning, testing or curing water, air or soil conditions and/or associated equipment). The tasks can represent routinely scheduled tasks (e.g., periodic inspections or testing) and reactive tasks which are prompted in response to detecting hazardous or potentially hazardous environmental conditions (e.g., using monitoring and sensory equipment at the sites and/or data supplied by service providers). Automated remedial measures can be taken to cure the hazardous conditions (e.g., by remotely activating remediation equipment at the sites and/or scheduling service providers). The platform aggregates all of the information generated in connection with managing the environmental conditions at the various sites and utilizes the aggregated information to predict occurrences of hazardous environmental conditions at the sites.

In another particularly useful application, the platform is additionally or alternatively configured to provide assistance associated with executing integrated facilities management (IFM) operations and tasks. The platform permits the property managers to schedule, manage, monitor and verify tasks associated with interior property services (e.g., building maintenance, plumbing services, electrical services, HVAC services, computer services, and/or cleaning services), exterior property services (e.g., construction projects, snow removal and landscaping services), safety conditions (e.g., related to safety measures associated with protection against fires, earthquakes, tornados, or inclement weather), and other types of tasks associated with servicing sites, facilities or even individual property owners or consumers. The platform can additionally be configured to provide assistance with fulfilling compliance obligations associated with various property-related governmental regulations (e.g., housing regulations, zoning regulations, and/or regulations pertaining to landlords). The tasks include routinely scheduled tasks (e.g., periodic maintenance) and reactive tasks which are prompted in response to detecting certain conditions (e.g., detecting malfunctioning or damaged structures/devices requiring repair services and/or detecting weather conditions which require snow removal services). Automated remedial measures are taken to cure or address the conditions (e.g., by remotely activating remediation equipment at the sites and/or scheduling service providers). The platform aggregates all of the information generated in connection with managing the conditions at the various sites and utilizes the aggregated information to predict occurrences of unfavorable conditions at the sites.

The platform and related features described in this disclosure provide numerous advantages over prior art techniques for ensuring compliance with environmental and facilities management obligations. In contrast to the error-prone and labor-intensive methods that rely heavily on property managers' individual or manual efforts to track compliance with the regulations and obligations, the platform described herein provides a centralized system which is able to simultaneously monitor compliance issues for a plurality of sites, communicate between various stakeholders, notify property managers of actions or tasks that should be handled at the sites, and continuously update the statuses of the sites. The process of scheduling a service provider to handle such actions or tasks is also expedited and simplified by the tools available via the communications framework of the platform, which enable the property managers to instantly contact and/or schedule any of a plurality of certified vendors. Reducing the time required to identify and mitigate hazards and/or other unfavorable conditions at sites, or eliminating such conditions before they arise, is extremely important given that failure to do can result in harm or death to individuals located at the sites.

The inventive principles set forth in the disclosure provide the above-described advantages by applying technical improvements that are rooted in computer and sensory technologies to overcome existing problems associated with ensuring compliance with regulations or other obligations, specifically problems dealing with the monitoring of environmental and facilities management conditions and automating the handling of tasks at sites. These technological improvements provide a centralized platform that is able to simultaneously monitor environmental, facilities management conditions, and other conditions (e.g., using networked sensory and monitoring equipment which can detect hazardous/unfavorable conditions in real-time and/or using monitoring information supplied by service providers) at a plurality of sites, remotely activate equipment at sites to take corrective measures when unfavorable conditions are detected, interconnect users instantly via a communication framework for handling detected conditions or compliance tasks, and automatically generate alerts in response to detecting triggering events that indicate actions should be taken at the sites. The platform is further outfitted with technological improvements that are able to provide predictions or recommendations for avoiding hazardous or other unfavorable conditions at the sites and/or utilizing appropriate compliance measures. This technology-based solution marks a technical improvement over capabilities for ensuring compliance with environmental regulations and facilities management obligations by improving the manner in which unfavorable conditions are detected and handled at the sites.

The embodiments described in this disclosure can be combined in various ways. Any aspect or feature that is described for one embodiment can be incorporated into any other embodiment mentioned in this disclosure. Moreover, any of the embodiments described herein may be hardware-based, software-based and, preferably, comprise a mixture of both hardware and software elements. Thus, while the description herein may describe certain embodiments, features or components as being implemented in software or hardware, it should be recognized that any embodiment, feature or component that is described in the present application may be implemented in hardware and/or software. In certain embodiments, particular aspects are implemented in software which includes, but is not limited to, firmware, resident software, microcode, etc.

Embodiments may include a computer program product accessible from a computer-usable or computer-readable medium providing program code for use by, or in connection with, a computer or any instruction execution system. A computer-usable or computer-readable medium may include any apparatus that stores, communicates, propagates or transports the program for use by, or in connection with, the instruction execution system, apparatus, or device. The medium can be a magnetic, optical, electronic, electromagnetic, infrared, or semiconductor system (or apparatus or device) or a propagation medium. The medium may include a computer-readable storage medium such as a semiconductor or solid state memory, magnetic tape, a removable computer diskette, a random access memory (RAM), a read-only memory (ROM), a rigid magnetic disk and an optical disk, etc.

A data processing system suitable for storing and/or executing program code may include at least one processor coupled directly or indirectly to memory elements through a system bus. The memory elements can include local memory employed during actual execution of the program code, bulk storage, and cache memories which provide temporary storage of at least some program code to reduce the number of times code is retrieved from bulk storage during execution. Input/output or I/O devices (including but not limited to keyboards, displays, pointing devices, etc.) may be coupled to the system either directly or through intervening I/O controllers.

Network adapters may also be coupled to the system to enable the data processing system to become coupled to other data processing systems or remote printers or storage devices through intervening private or public networks. Modems, cable modems and Ethernet cards are just a few of the currently available types of network adapters.

FIG. 1 is a block diagram of a system 100 according to certain embodiments. A platform hosting device 130 includes a communications and monitoring platform 150 provides a comprehensive set of tools for preventing, mitigating and/or remediating occurrences of unfavorable conditions (e.g., hazardous biological/chemical conditions or facilities management conditions) at one or more sites 120.

In this exemplary system, one or more of the sites include cooling towers 121 or water towers 121. The platform hosting device 130 is in communication with the sites 120 over a network 190. The platform hosting device 130 is also in communication with one or more user devices 110 which are operated by various stakeholders such as site/facility/building managers, service providers/vendors, property owners, platform administrators and other individuals.

In certain embodiments, the platform 150 represents a network-based, web-based or cloud-based platform that is accessed over the network 190 by the user devices 110 operated by the stakeholders The network 190 can be any type of network such as one that includes the Internet, a local area network, a wide area network, an intranet, and/or other network. The platform 150 is hosted on one or more servers, or other devices, which are configured to communicate with the user devices 110 and the sites 120 (e.g., communicate with servers 122, monitoring equipment 124, and remediation equipment 126, sensors 128 and/or other devices located at the sites 120). The user devices 110, site servers 122 and platform hosting devices 130 may represent desktop computers, laptop computers, mobile devices (e.g., cell phones, smart phones or personal digital assistants), tablet devices, wearable devices (e.g., smart watches, smart glasses, etc.) or other types of computing devices. The user devices 110, sites 120, servers 122, monitoring equipment 124, remediation equipment 126, sensors 128, and platform hosting devices 130 can be configured to communicate via wired or wireless links, or a combination of the two. These components can communicate directly with one another and/or via the network 190. Each may be equipped with one or more computer storage devices (e.g., RAM, ROM, PROM, SRAM, etc.) and one or more processing devices (e.g., central processing units) that are capable of executing computer program instructions. The computer storage devices are preferably physical, non-transitory mediums.

In certain embodiments, the computer storage devices of the platform hosting device 130 are configured to store data, applications, scripts, databases and/or other information for implementing any and all functions described herein, including functions for implementing the communications framework 151, alert generator and transmitter 152, reporting component 153, databases 154, data analyzer and prediction component 155, remediation component 156, and other related features described in this disclosure. The user devices 110 operated by the property managers, service providers and other users can include software applications that communicate with the platform 150 to access the data, applications, scripts, databases 151, interfaces and/or other information on the platform hosting device 130. The software applications can also enable the user devices 110 to access the sites 120 (including all of its components) via the platform 150 and/or directly in order to remotely access and control the monitoring equipment 124 and remediation equipment 126. In certain embodiments, the platform 150 is alternatively, or additionally, implemented as a local application that is installed on the user devices 110 operated by the users or site servers 122.

In certain embodiments, the property or facility managers access the platform 150 to receive alerts for determining whether tasks need to be scheduled (e.g., for complying with environmental regulations or facilities management obligations), checking statuses of upcoming or scheduled tasks, curing unfavorable conditions, and for other reasons. In certain embodiments, the scheduling of tasks is based on obligations imposed by regulatory compliance measures (e.g., which require property managers to periodically check certain environmental conditions at sites) and/or facilities management obligations. The platform 150 stores data, information, software and/or scripts for identifying any relevant deadlines, tasks or actions that should be taken in connection with fulfilling the obligations. The scheduling of tasks can also be initiated by the detection of unfavorable or potentially unfavorable conditions at the sites. The detection of such conditions can be performed by in-person inspections performed by service providers and/or automatically by monitoring equipment located at the sites (e.g., which include sensor devices configured to detect biological or chemical substances in the water or air supply at the sites).

The platform 150 includes an alert generator and transmitter 152 which automatically transmits notifications or alerts to user devices 110 operated by property managers, vendors and/or other users at any appropriate time to notify the users of any events which require their attention. In certain embodiments, the alert generator and transmitter 152 is configured to automatically detect when environmental tasks should be performed or scheduled, when property managers are delinquent on their obligations to perform environmental tasks, and/or when unfavorable conditions are present at sites. The alert generator and transmitter 152 transmits notifications to the users in the event that any such events are detected.

In certain embodiments, the alert generator and transmitter 152 transmits notifications to user devices 110 operated by property managers in response to identifying the presence of unfavorable environmental conditions associated with water, air and/or soil quality at one or more sites. For example, notifications are transmitted to managers in response to detecting unacceptable legionella or biological agents in water supplies located at the sites 120. For embodiments in which the platform 150 is configured to provide assistance with IFM operations, the alert generator and transmitter 152 transmits notifications to user devices 110 in response to detecting unfavorable conditions or conditions which require attention. For example, notifications can also be transmitted in response to detecting weather conditions, suspicious security activities, building maintenance issues (e.g., associated with electrical, plumbing, HVAC, etc.), or other conditions which require the attention of a property manager.

The platform 150 stores a set of rules and event triggers that can immediately activate the sending of notifications, initiate a series of corrective measures, and/or perform other related functions. For example, in the event that the platform 150 receives an indication that unsatisfactory laboratory results have been obtained in connection with legionella testing (or other biological/chemical testing), the platform can be configured to initiate a series of corrective measures (e.g., setting deadlines to correct measures, scheduling appropriate vendors for treating water, and scheduling a laboratory to analyze the treated water). Likewise, in response to detecting broken HVAC system, the platform 150 can be configured to initiate a series of corrective measures for notifying tenants/occupants of conditions, scheduling HVAC repair services, reserving alternative space in the building for the tenants/occupants while repairs are ongoing, etc. Any corrective measures taken by the platform 150 can be performed automatically by the platform 150 and/or with the assistance of an individual (e.g., property manager). The platform 150 can utilize the rules and triggers to perform similar actions in other scenarios involving other types of events.

The property managers utilize the communications framework 151 to select one or more vendors for completing the tasks. For example, the communications framework 151 presents vendor information that identifies the name of the service providers, types of services offered by the service providers, pricing information associated with the service providers, contact information for the service providers, prior experience information indicating which service providers have been previously utilized by the property managers, ratings and reviews of prior experiences with the vendors, locations of the service providers, availability of the service providers and any other information related to the service providers. All of this information is stored in the database 154. The property managers utilize the vendor information to select appropriate service providers to execute the tasks. To assist with the selection process, the platform 150 enables the property managers to specify selection or filtering criteria based on the service providers' ratings, certifications (e.g., indicating whether or not the service providers are certified to perform certain compliance tasks such as laboratory testing or water treatment tasks), insurance availability, locations or other criteria.

Generally speaking, the service providers listed on and made available via the platform can perform any task desired by the property managers. For example, in the context of ensuring compliance with environmental regulations pertaining to water towers or cooling towers 121, the vendors can be utilized to perform tasks related to treating and cleaning water, cleaning water tower structures, applying pesticides or disinfectants, supplying laboratory results (e.g., which provide an analysis of biological or chemical parameters present in the water), draining and filling the tower structures, and performing maintenance on the tower structures or water systems. The service providers scheduled through the platform 150 can perform tasks related to ensuring compliance with other types of environmental regulations (e.g., relating to asbestos, mold, etc.). The service providers scheduled through the platform 150 can also perform tasks related to facility management operations such as tasks associated with building maintenance, cleaning services, construction services, computing services, snow removal services, security services, etc.

The communications framework 151 permits property managers and service providers to quickly and easily communicate for scheduling service providers to perform assignments, verify completion of tasks assigned to service providers, and for other related purposes. The communications framework 151 includes tools which permit the property managers and service providers to communicate through the platform (e.g., via inbox messages, instant messaging, etc.) and/or by other communication means (e.g., by telephone, fax or e-mail). The communications framework 151 also provides interfaces which permit the property managers and service providers to communicate for various purposes related to fulfilling tasks. For example, the interfaces permit the property managers to transmit requests for services to service providers, and permit the service providers to confirm or deny the requests. The interfaces further display statuses of tasks throughout their lifecycle, and enable service providers to upload or supply verification data (e.g., photos, laboratory results, certifications, documents or other information) to confirm whether or not tasks have been completed. All of this monitoring information is stored in the database 154.

In certain embodiments, the communications framework 151 includes a crowd sourcing component that permits property managers to quickly select and assign service providers to complete tasks. This crowd sourcing component is configured to simultaneously transmit requests to a plurality of service providers to determine their availability and costs for completing tasks. The crowd sourcing component may rank or prioritize service providers based on aggregated ratings provided by other property managers who have utilized the vendor in the past, filtering criteria provided by the property manager (e.g., which may be based on distance, availability, pricing or ratings associated with the service providers), and/or other factors.

In certain embodiments, the platform 150 further includes a reporting 153 component that is configured to communicate with third-party systems associated with governments, compliance enforcement authorities or the like. For example, the reporting component can be configured to communicate directly with these third parties via application programming interfaces (API) in order to provide indications and/or documentation for verifying compliance with various environmental regulations, to pay any associated fees (e.g., resulting from violations of the environmental regulations) and/or for other related purposes. The reporting component 153 is also configured to generate reports and/or packages of information including compliance documentation in appropriate formats and having the necessary information. The reporting component can also generate reports and/or packages of information related to completed and scheduled facilities management operations. The reporting component stores and retains records (e.g., in database 154) for later retrieval by users. In certain embodiments, the reporting component is configured to delete records after they are retained for a predetermined period of time (e.g., 1 year or 3 years) to comply with document retention obligations.

The platform 150 can be configured for use with facilities management software applications and systems which can provide assistance with maintenance and other site services, computer-aided facility management (CAFM) software and systems which can provide various forms of information technology pertaining to the sites, building automation systems (BAS) and software which automate various aspects of a building (e.g., a building's heating, ventilation and air conditioning, lighting and other systems) and/or any other type of system or software application that provides assistance with managing a site 120. The platform 150 can be directly integrated and packaged with such systems or software applications, or can communicate with such systems and software applications (e.g., via an API).

The platform 150 includes a data analyzer and prediction component 155 which is configured to analyze and process the data stored on the platform and/or database 154 (e.g., which may include any data associated with conditions at the sites, property managers, vendors, tasks, statuses of tasks, adherence to compliance regulations, unfavorable conditions that were detected, and any other information mentioned herein) to provide predictions or recommendations for various purposes. In certain embodiments, the data analyzer and prediction component 155 is configured to generate scores for each site 120 (and/or for each of the property managers) that indicate if the properties are being managed in a manner that is in compliance with the relevant standards, such as environmental regulations or facilities management obligations. For example, the score associated with a site 120 may be negatively affected if one or more environmental tasks or facilities management tasks have not been performed or scheduled in a timely manner, or if unfavorable conditions are detected at the site 120. On the other hand, the score associated with a site may be positively affected if the platform 150 is provided with confirmations that environmental tasks and/or facilities management tasks have been performed or if the platform detects or confirms that unfavorable conditions at the site have been mitigated or cured. A property manager is able to access an interface which displays a listing of all sites the manager is overseeing and the associated scores for each site 120 to enable the manager to instantly determine which sites 120 require attention (e.g., to identify sites where environmental tasks should be implemented).

The data analyzer and prediction component 155 is further configured to identify, monitor and display trending information associated with users (e.g., property managers) or sites 120. For example, the data analyzer and prediction component indicates whether users or sites 120 are trending upward or downward in terms of satisfying their compliance or facility management obligations. Users and sites 120 will trend upward in the event that they are doing a better job fulfilling their obligations (e.g., reducing the number of violations or handling tasks more quickly) than they had previously, or downward in the event that they are doing a worse job of fulfilling their obligations than they had previously. The data analyzer and prediction component 155 also indicates whether users and sites 120 are trending upward or downward with respect to other users and sites 120 (e.g., other users or sites in the same geographic area or all other users or sites registered on the platform). Users will trend upward if they are satisfying compliance or facilities management obligations better than the majority (or a subset) of other users, or will trend downward if they are not satisfying such obligations better than the majority (or a subset) of the users. The trends identified by the data analyzer and prediction component 155 may be based, at least in part, on the scores generate for the users and sites 120.

The data analyzer and prediction component 155 can also be configured to generate graphs, charts, and visual presentations which summarize various information pertaining to the property managers, service providers, tasks, adherence to compliance regulations, industry metrics or any other related information. For example, the data analyzer and prediction component is configured to generate charts or graphs for each site 120 that illustrate how the score assigned to the site has progressed over the course of a certain time period (e.g., a month or year) in a comparison to other sites 120 that are managed by the platform 150 and/or other sites 120 that are in within the same industry.

The data analyzer and prediction component 155 is also configured to perform data mining and analytics operations on the data stored on the platform 155 to make predictions regarding compliance trends, occurrences of unfavorable conditions, and related issues. For example, the data analyzer and prediction component 155 can analyze aggregated historical data pertaining to detection of prior unfavorable conditions at sites 120 to predict the occurrence of future unfavorable conditions. Similarly, the data analyzer and prediction component 155 can analyze historical data associated with prior remediation efforts to predict or recommend optimal service providers or optimal remediation options for treating existing or potential unfavorable conditions. The data analyzer and prediction component 155 analyzes the data stored on the platform 150 to provide other types of recommendations and predictions as well. The alert generator and transmitter 152 communicates with the data analyzer and prediction component 155 to transmit alerts over the network 190 which notify the property managers, service providers or other users of any relevant recommendations or predictions. In certain cases, the alerts can provide warnings regarding predicted environmental hazards (e.g., predict legionella outbreaks or occurrences) or unfavorable conditions associated with facility management services (e.g., elevator or HVAC repair measures) which require corrective measures.

The data analyzer and prediction component 155 utilizes any data associated with the sites 120 to make the predictions and recommendations. The data analyzer and prediction component 155 can also utilize data from third-parties (e.g., weather services, governmental databases/records, etc.) to make the predictions and recommendations. For example, the data analyzer and prediction component predicts future occurrences of unfavorable conditions (e.g., hazardous or non-complying conditions) by analyzing aggregated historical data that indicates weather conditions (e.g., external temperatures, humidity levels, precipitation levels, etc.) present during previous occurrences of such conditions, equipment located (e.g., HVAC equipment) at sites where the unfavorable conditions occurred, geographic patterns associated with the occurrences of the unfavorable conditions, service providers used to prevent or treat conditions at the sites where the unfavorable conditions occurred, and/or any other historical data. In certain embodiments, the data analyzer and prediction component 155 is configured to analyze historical data associated with multiple sites to detect patterns associated with elevated levels of unfavorable conditions (e.g., elevated levels of legionella, bacteria or other biological/chemical agents) and to recommend preventative measures for avoiding the unfavorable conditions. Any other predictions and recommendations made by the data analyzer and prediction component 155 can be based, at least in part, on the analysis of the above-mentioned historical data or other types of data.

As mentioned above, in certain embodiments, the platform 150 communicates with monitoring equipment 124 located at the sites 120 to determine whether unfavorable or potentially unfavorable conditions exist at the sites 120 and/or to determine whether service providers should be scheduled to perform tasks at the sites 120. The monitoring equipment 124 can be configured to detect the presence of hazardous or unfavorable conditions at the sites utilizing sensors, analysis hardware or software, and/or associated devices and circuitry. For example, the monitoring equipment 124 at a site 120 may include devices that include sensors and/or analysis software for detecting the presence or potential presence of biological or chemical hazards, acidity conditions, weather conditions, and/or equipment functionality (e.g., HVAC, computing, electrical or plumbing equipment functionality). Analog inputs received via the sensors can be converted to digital signals and evaluated by the analysis software to detect the presence of such hazards or unfavorable conditions. In response to detecting an unfavorable or potentially unfavorable condition at a site 120, the monitoring equipment 124 transmits a signal (using wired or wireless communication techniques) over the network 190 to the platform 150 and site server 122. The alert signal can then be relayed to one or more user devices 110 to notify the associated property manager (or other individuals) of the detected condition. The alert generator and transmitter 152 can send the appropriate notifications to the property manager, property owner and/or other individuals associated with the site 120. In this manner, the platform 150 provides real-time monitoring of environmental and facility conditions at the sites and allows the property managers to immediately take remediation actions to cure the conditions. In certain embodiments, in response to the monitoring equipment 124 detecting an unfavorable condition at a site, the ruleset stored on the platform 150 triggers the platform 150 to automatically present the property manager with a series of corrective measures and the system identifies and stores appropriate deadlines, task information, and related data for curing the condition.

The remediation component 156 of the platform 150 is configured to execute a variety of actions for curing, mitigating or remediating unfavorable conditions at the sites 120. In certain embodiments, the remediation component 156 is configured to control and utilize remediation equipment 126 to cure or prevent unfavorable conditions at the sites 120. Generally speaking, the remediation equipment 126 can represent any device capable of providing assistance with preventing unfavorable conditions at a site 120. Exemplary remediation equipment 126 includes equipment for treating water (e.g., by treating the water with biocides, filters or in other ways), air, soil or other environmental aspects at the sites 120. Other types of remediation equipment 126 can include facilities management equipment such as automated snow removal devices, automated floor cleaning devices (e.g., autonomous robotic cleaners that scrub, vacuum, sweep or otherwise clean floors), and other types of automated facilities management devices. In certain embodiments, the remediation equipment 126 includes one or more sensors 128 for monitoring conditions. Any type of sensor 128 can be used. The remediation equipment 126 (and/or sensors 128) is in communication (e.g., via wired or wireless communication) with the platform 150, site servers 122 and/or monitoring equipment 124, and can be activated automatically (e.g., in response to the monitoring equipment detecting an unfavorable condition) or in response to a platform user selecting activation options that are made available via the platform 150.

The remediation component 156 provides the user with controls (e.g., which are displayed on an interface of the user device 110) for activating/de-activating the remediation equipment 126 and for controlling the remediation equipment 126 in various ways. The remediation component 156 provides a customized set of controls for each device included with the remediation equipment 126 which take advantage of the hardware and functionality of devices. For example, if water treat equipment is made available at a site 120, the remediation component 156 can provide a user with controls for selecting biocides and disinfectants to be administered, specifying levels of biocides or disinfectants to be applied, specifying filtration parameters, specifying maximum acceptable contaminant levels, and any other parameters associated with treating water. Likewise, if an autonomous floor cleaning device is provided at a site 120, the controls can allow locations that require cleaning to be specified, along with the type of cleaning (e.g., scrubbing cleanse, vacuum cleanse, soap cleanse, etc.) to be performed at the locations. Appropriate controls can be customized for each of the devices included in the remediation equipment 126.

Figure 2:
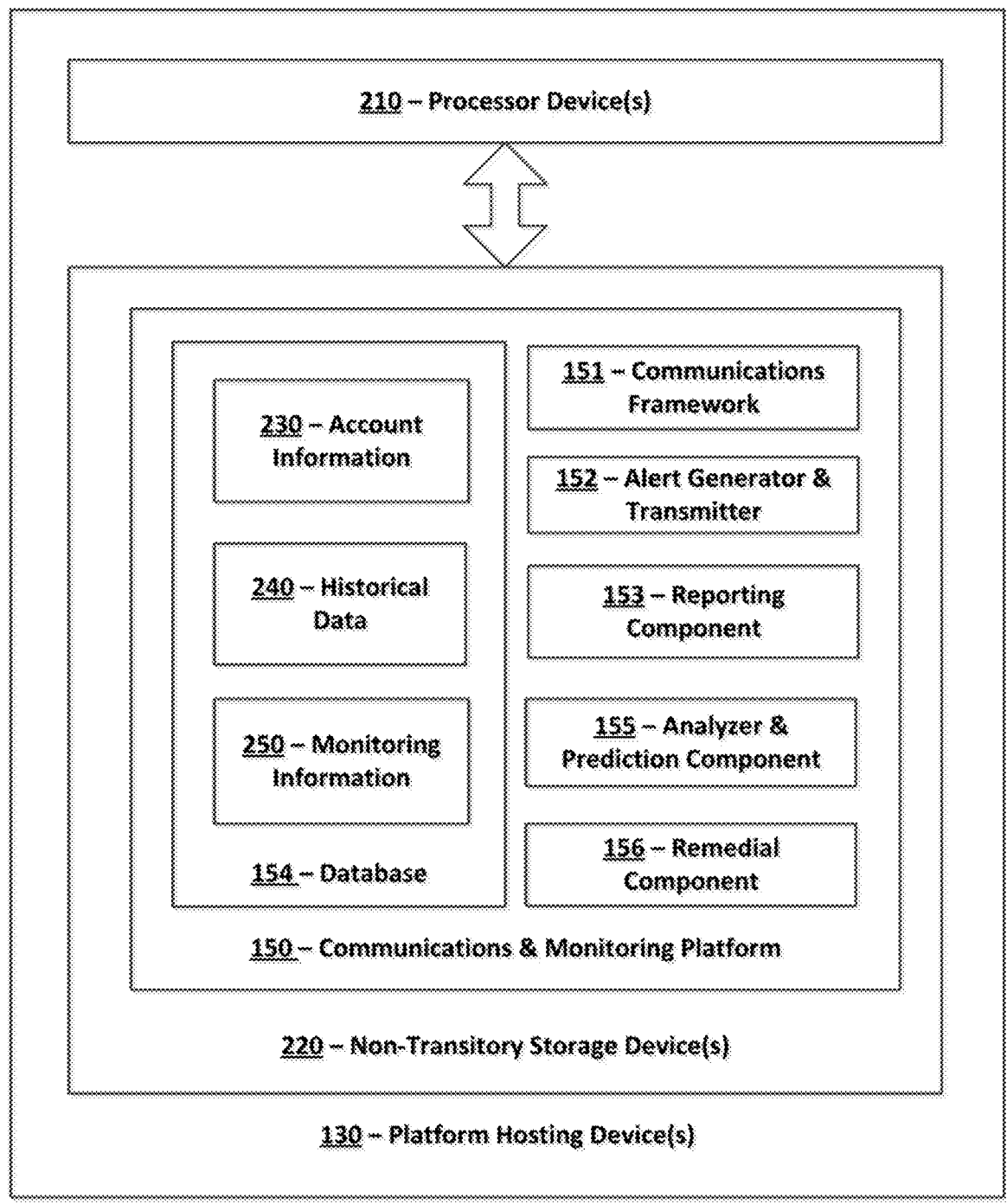
FIG. 2 is a block diagram which provides a detailed view of a platform hosting device according to certain embodiments.

FIG. 2 is a block diagram which provides a detailed view of a platform hosting device 130 according to certain embodiments. The platform hosting device 130 includes one or more processor devices 210 (e.g., CPUs) and one or more non-transitory computer storage mediums 220. The communications framework 151, alert generator and transmitter 152, reporting component 153, databases 154, data analyzer and prediction component 155, and remediation component 156 are stored on the non-transitory storage medium 220 and their associated instructions are executed by the processor device 210. The database 154 stores account information 230, historical data 240, monitoring information 250, and rules 260.

In certain embodiments, the platform 150 permits accounts and associated profiles to be created for different types of users including, but not limited to, property managers, service providers (or vendors) and administrators. Any information associated with the user accounts is stored in the account information 230 in the database 154. Generally speaking, the property managers represent owners, facilities managers, tenants or any of their representatives whereby individual users are responsible for overseeing sites 120, including ensuring regulatory compliance (e.g., with environmental laws) at one or more sites 120, performing facilities management operations, and/or attending to other issues at the sites 120. The service providers represent any person or entity who can be hired and/or assigned to perform tasks associated with fulfilling compliance obligations, facilities management obligations, or other types of tasks. Administrators represent any users associated with managing, maintaining and/or providing the platform 150. The platform 150 stores any data associated with each of these users in the account information 230 and provides appropriate interfaces to the users for performing any the functions mentioned in this disclosure.

The platform 150 present interfaces that display appropriate forms to register each of the users. For example, when a property manager signs up for an account on the platform, the platform 150 can present the property manager with forms for identifying contacts at the sites 120, specifying one or more service providers for performing particular types of tasks, and/or other related information. Likewise, when a service provider registers with the system, the service provider can be presented with forms for specifying certifications, identifying tasks that the service provider can perform, identifying availability information, etc. Once the users are registered, they can login and access the platform 150 using the user devices 110.

The monitoring information 150 can include any data associated with monitoring the sites 120. For example, the monitoring information 150 can include any data that is generated by the monitoring equipment 124 (e.g., including real-time monitoring data), as well as any data that is provided by the service providers in connection with performing tasks at the sites 120. For example, the monitoring information 150 can include any data indicating the statuses of conditions at the sites 120 (e.g., indicating site status is in good condition, poor condition, hazardous, etc.), any data associated with testing (e.g., laboratory testing results or on-site testing results), any data associated with inspections at the sites, any data associated with regulation compliance, any dates/times indicating when tasks were started/completed, any data associated with unfavorable conditions detected at sites, any data associated with service providers who performed tasks at the site, etc.

The historical data 240 is a vast data collection which comprises any previously recorded monitoring information 150 for the sites 120, as well as a variety of other data points. For example, the historical data 240 can include previously recorded data such as data relating to previous weather conditions at the sites 120, geographic locations of sites 120, data associated with detection of unfavorable conditions at the sites 120, data associated with equipment used at the sites (e.g., water treatment equipment, monitoring equipment 124, remediation equipment 126, facilities management equipment, etc.), data associated with service providers used at the sites (e.g., indicating which providers serviced sites, types of tasks performed by providers, dates tasks or sub-tasks were started and completed, etc.), data associated with previous tests conducted (e.g., laboratory testing of legionella, biological/chemical agents, etc.), previous fines imposed for violating compliance regulations, data pertaining to outbreaks caused by chemical or biological agents (e.g., legionella outbreak information), data associated with equipment failure at the sites 120, data associated with the scores generated for the sites, data associated with events (e.g., political or social events) that occurred previously, and any other related data, data received from third-party entities (e.g., weather or government databases), and any other related data.

Figure 3A:
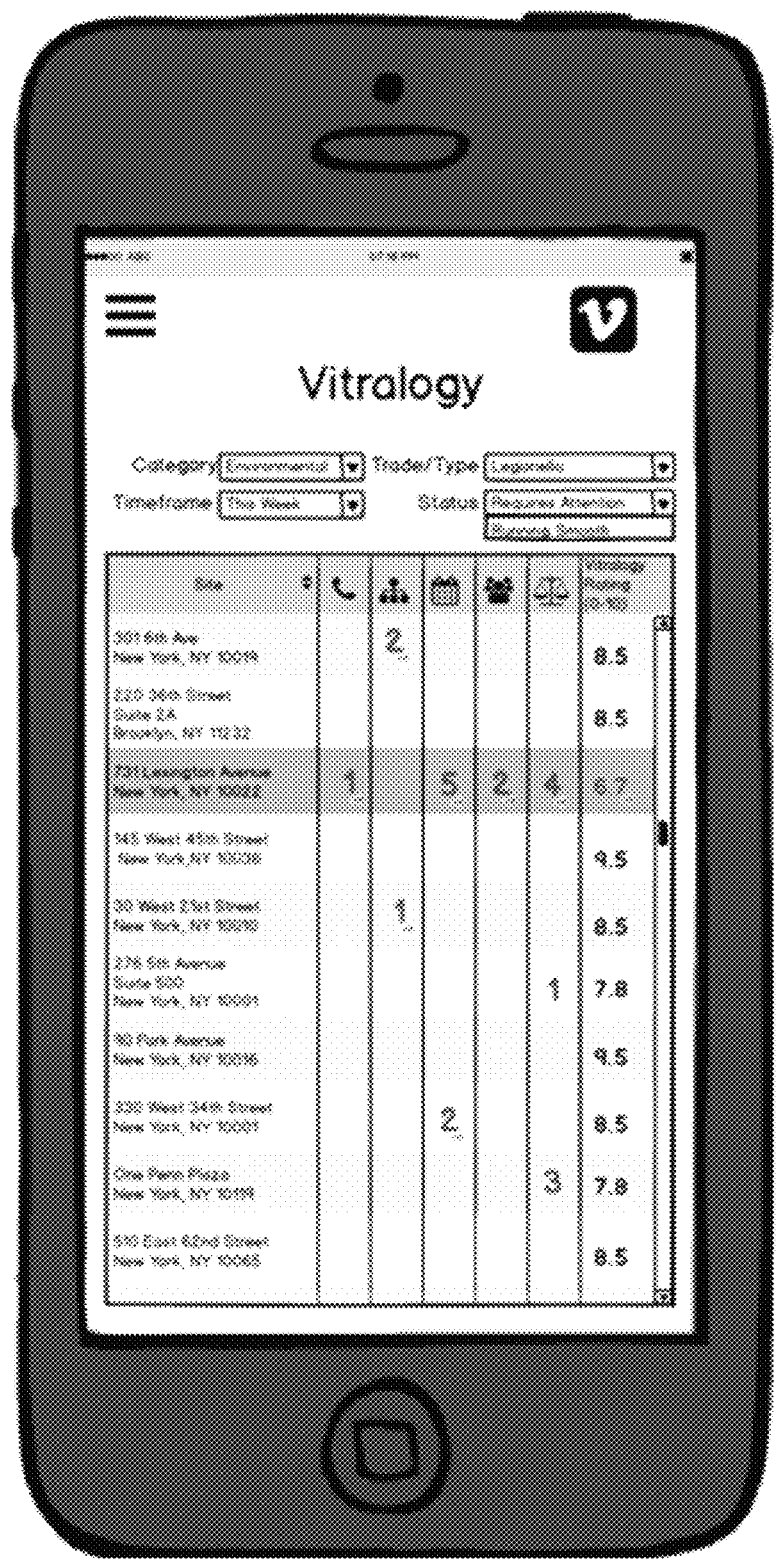
FIG. 3A-3N are illustrations of exemplary interfaces provided by the monitoring and communications platform to assist property managers with handling environmental compliance associated with water or cooling towers in accordance with certain embodiments.
Figure 3B:
FIG. 3B is an illustration of an exemplary contact interface that provides information associated with service providers.
Figure 3E:
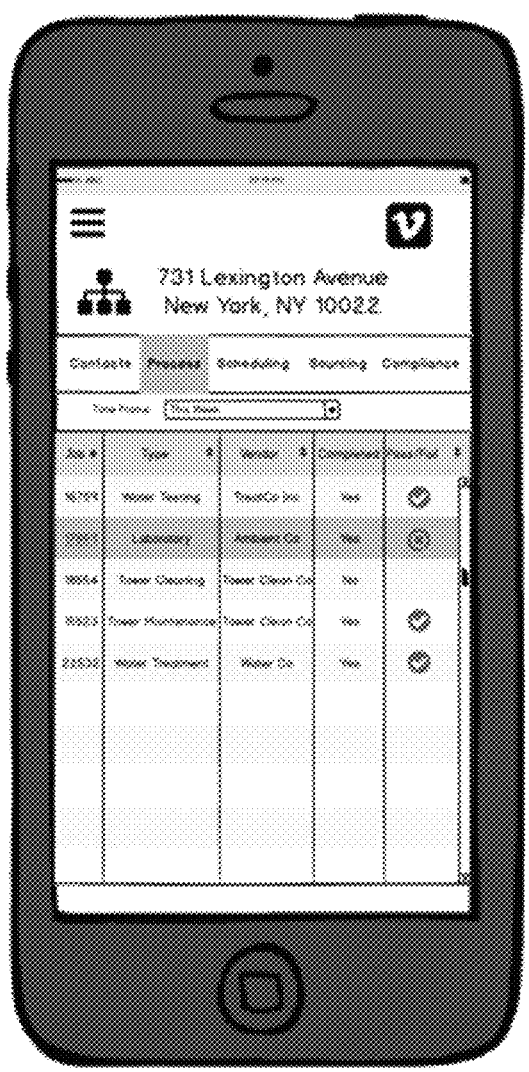
FIG. 3E is an illustration of an exemplary process interface that displays a listing of exemplary compliance tasks.
Figure 3F:
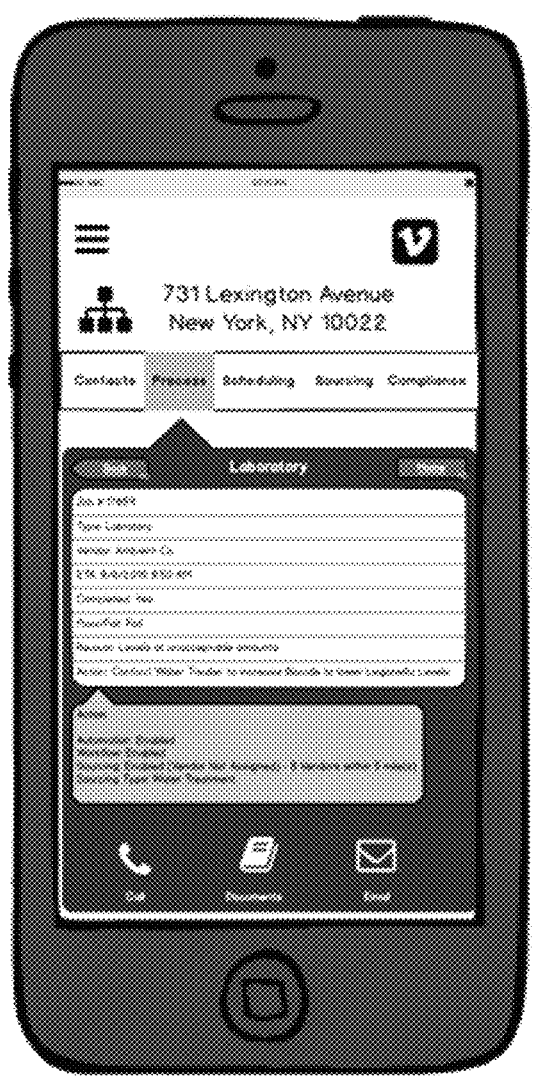
FIG. 3F is an illustration of an exemplary process details interface that displays additional details about the performance of the task.
Figure 3I:
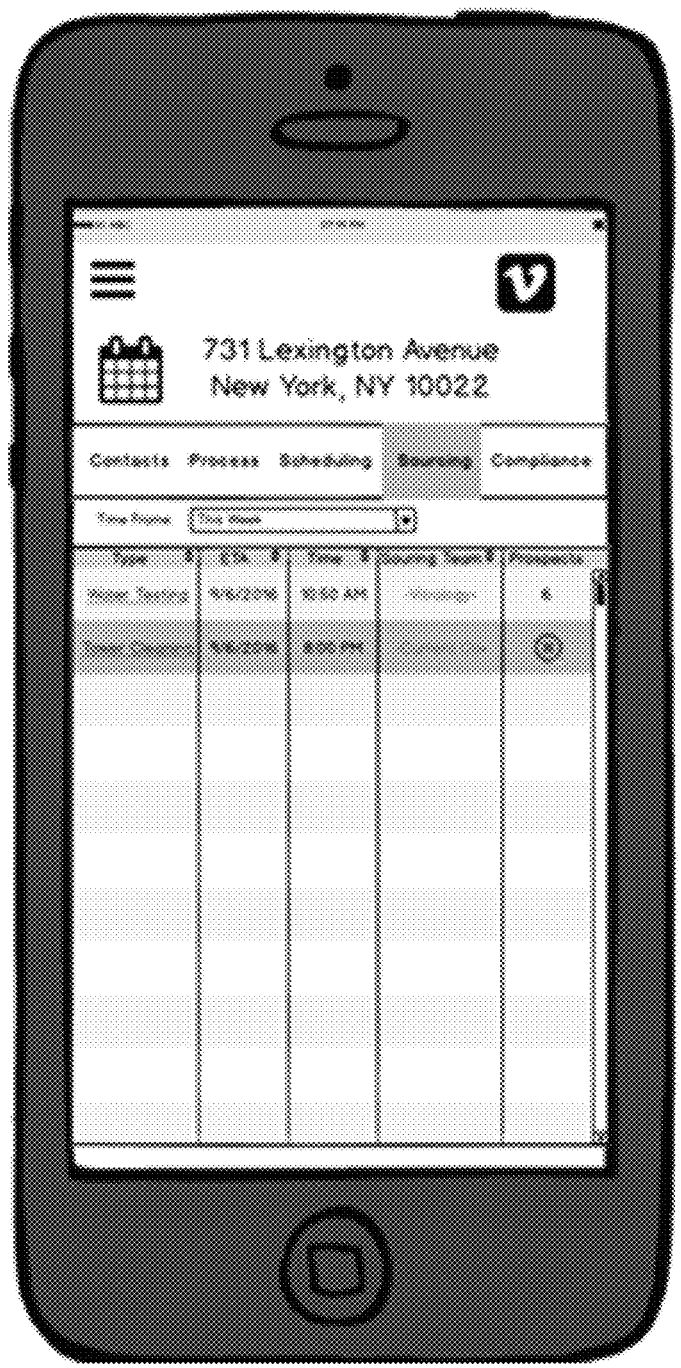
FIG. 3I is an illustration of an exemplary sourcing interface that displays information related to service providers assigned to tasks.
Figure 3L:
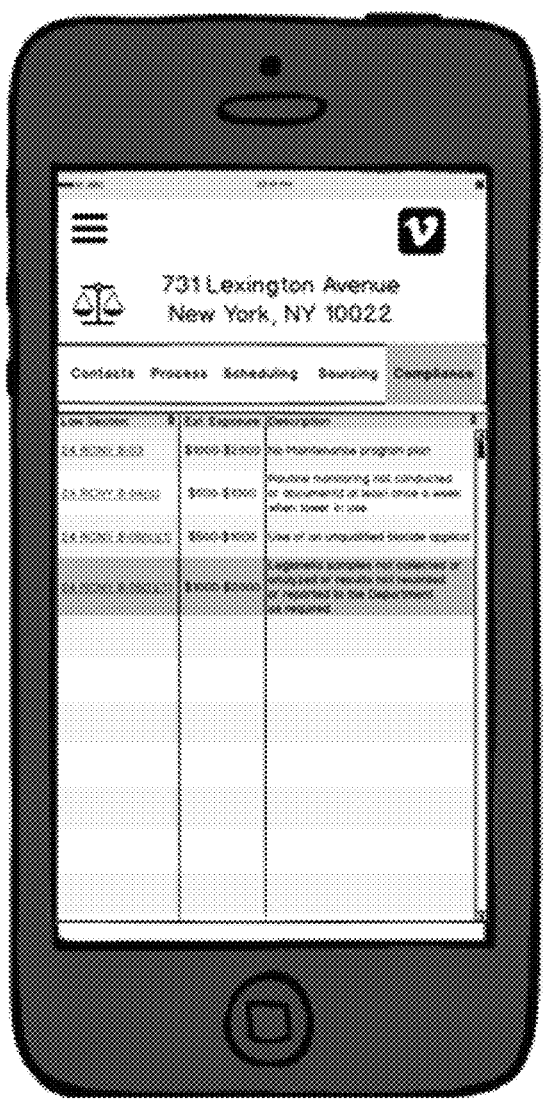
FIG. 3L is an illustration of an exemplary compliance interface that includes a listing of potential violations that may apply to the associated site.
Figure 3M:
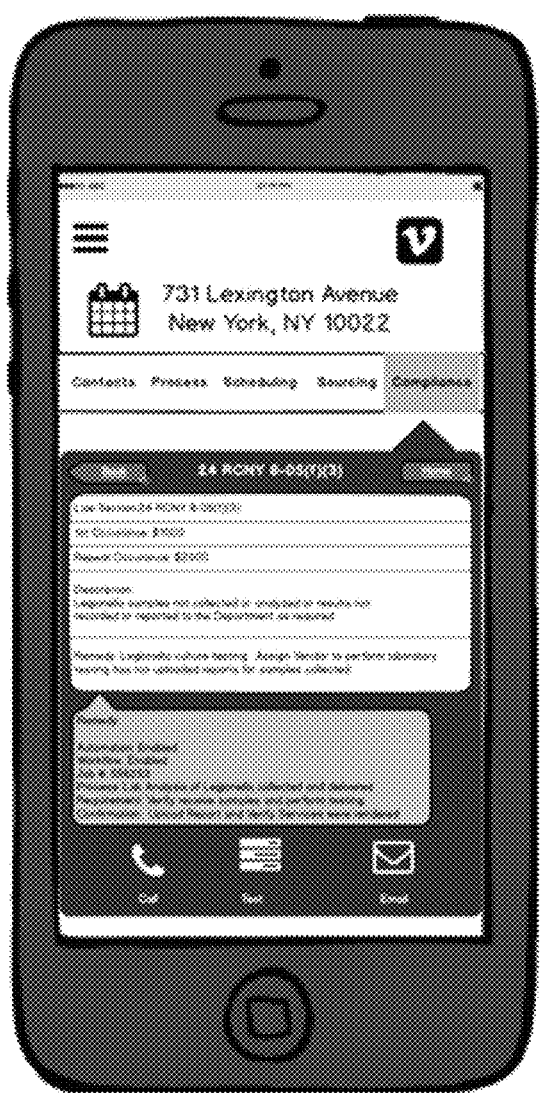
FIG. 3M is an illustration of an exemplary compliance details interface that includes additional details pertaining to a potential violation.
Figure 3N:
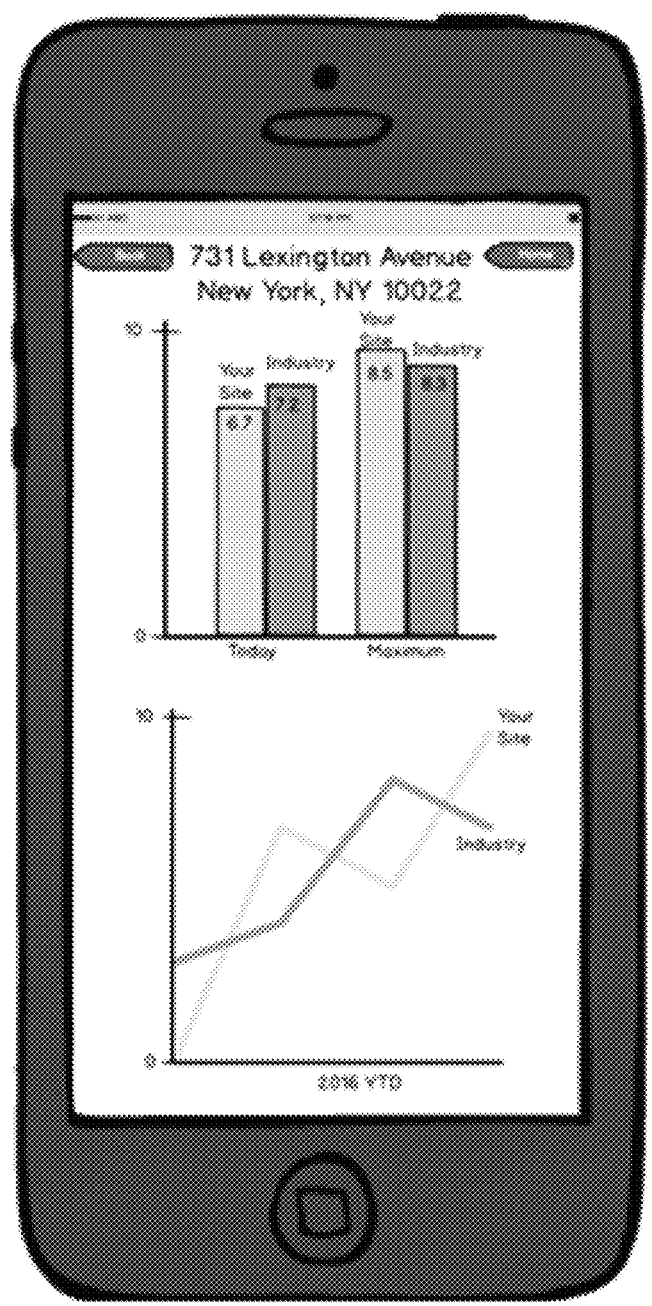

FIGS. 3A-3N illustrate exemplary interfaces that are provided by the monitoring and communications platform 150 on user devices 110 to property managers or other users. The interfaces provide assistance, inter alia, with fulfilling obligations associated with environmental regulations addressing water or cooling towers.

FIG. 3A is an illustration of an exemplary management interface 300A displayed on a mobile device which enables a property manager to manage compliance obligations associated with regulations pertaining to water or cooling towers for a plurality of sites 120. The top of the interface includes several selectable menus and the bottom of the interface includes a table that provides a summary of information pertaining to the sites.

The selectable menus located at the top of the screen include the following:

(a) Category Menu Option: This menu option indicates the general class or category of information which is displayed in the table below the menu options. The current selection is "Environmental" indicating that the type of information being displayed in the table pertains to information that is relevant to environmental regulations or operations. The user selects this menu option to change the current selection. Other exemplary selections can pertain to categories for non-environmental regulations (e.g., housing regulations), building/facility maintenance operations, facility construction operations, interior services (e.g., HVAC, electrical or plumbing services), exterior services (e.g., snow removal or construction services), etc. The information in the table is updated to reflect information associated with the selected category.

(b) Trade/Type Menu Option: This menu option specifies a sub-category associated with the selected category. The current selection is "Legionella" indicating that the specific type of environmental information which is displayed in the table pertains to regulations that address legionella (such as those regulations which pertain to inspection and maintenance of water or cooling towers). The user selects this menu option to change the current selection. Other exemplary selections pertain to sub-categories of regulations pertaining to other types of environmental issues (e.g., asbestos, lead or radon levels). The information in the table is updated to reflect information associated with the selected sub-category.

(c) Timeframe Menu Option: This menu option specifies a timeframe which applies to the information which is displayed in the table. The current selection is "This Week" indicating that the table is displaying information for the current week. The user selects this menu option to change the current selection. The other selections available under this menu option permit the user to adjust the timeframe to any appropriate time frame (e.g., one month, six months or one year). The information in the table is updated to reflect the selected timeframe.

(d) Status Information Menu Option: This menu option specifies the status of information which is displayed in the table. The current selection is "Requires Attention" indicating that the table is displaying information for the properties listed in the tables which require attention within the specified timeframe. The user selects this menu option to change the current selection to "Running Smoothly," thus updating the table to display which properties do not currently require attention within the selected timeframe.

The table located below the menu options provides a summary of information pertaining to the sites 120 and includes the columns pertaining to the following categories described below (described in order from left to right).

(a) Property Identification: The first column in the table of FIG. 3A provides a listing of properties and includes information which identifies the name and/or address of the properties. These properties are included in a portfolio that is handled by a property manager. The property manager accesses its account on the platform 150 via the mobile device, or other user device 110, to manage compliance obligations with environmental regulations and/or to handle other issues related to these properties (e.g., scheduling maintenance works or managing compliance obligations associated with non-environmental regulations).

(b) Contact Info Status: This second column in the table of FIG. 3A will display an indicator in a row of a site 120 in the event that contact information is missing for a contact associated with the site 120 (e.g., a building superintendent, a building owner, a service provider or a facility manager). In the exemplary embodiment of FIG. 3A, the indicator is a numerical digit that falls within a pre-determined range (e.g., 1-5) and indicates how many issues must be addressed. Thus, when the indicator is "1" and is located in the contact info status column, this means there is one contact with missing information. The same applies to the indicators that are included in the other columns of the table which are discussed in further detail below.

FIG. 3B illustrates an exemplary contact interface 300B that is displayed in response to a user selecting an indicator in the second column of FIG. 3A. The interface indicates that contact information is missing for two contacts. The top of the interface displays a table that includes a listing of contacts for the site 120 associated with the selected indicator. The table identifies the role (e.g., building superintendent or building owner), company and responsibility of each contact included in the listing. The bottom of the interface displays a second table that includes a listing of service provider associated with the site 120. This display indicates the role, company, date of last visit and date of the next scheduled visit for each service provider. Both tables include a status column which indicates whether contact information has been provided for the contacts or service provider (i.e., with a check mark indicating that contact information has been provided and an "X" indicating that contact information has not been provided). The user selects an entry in either table to view, edit or input associated contact information.

FIG. 3C illustrates a contact details 300C interface that is displayed in response to selecting an entry in the contact listing that includes contact information for an individual or entity. The interface includes options for contacting the individual or entity (e.g., via phone or e-mail) and viewing a history log which stores information pertaining to prior communications with the individual or entity. FIG. 3D illustrates a similar contact details interface 300D that is displayed in response to selecting an entry in the contact listing that is not associated with contact information. The user utilizes this interface to input contact information. In response to updating the contact information, the status identifier for the entry (in the status column in FIG. 3B) is updated and the indicator in the second column of FIG. 3A is removed.

(c) Process Status: The third column in the table of FIG. 3A will display an indicator in a row of a site 120 in the event that a completed compliance task is not is insufficient (e.g., has failed inspection requirements, has failed testing requirements, requires a follow-up inspection or is otherwise defective). Again, the indicator specifies how many issues require attention. Thus, an indicator in this column specifies how many tasks were deemed to be insufficient. The user selects the indicator to access an interface that provides additional information regarding compliance tasks for the site 120.

FIG. 3E illustrates an exemplary process interface 300E that is displayed in response to a user selecting an indicator in the third column of FIG. 3A. The interface displays a table of exemplary compliance tasks associated with the "Category" and "Trade/Type" menu options specified in FIG. 3A. For each task, the table identifies an associated job number, task type, a service provider assigned to the task, and indication of whether the task has been completed. Thus, because these menu options are set to "Environmental" and "Legionella," the interface is displaying tasks related to complying with regulations associated with testing water or cooling towers for the presence of legionella. The tasks displayed and managed by this interface will vary based on the selected menu options. The table further includes a status column which indicates whether a completed task has passed inspection requirements or is otherwise satisfactory. This determination may be based, at least in part, on inputs received from the environmental service provider after completion of a task and/or automatically by monitoring equipment 124 located at the sites 120.

A user can select a task in the table to obtain additional details about the performance of the task. FIG. 3F illustrates an exemplary interface 300F that is displayed in response to selecting a completed task that was deemed to be unsatisfactory. The interface indicates why the task failed compliance obligations (in the row labeled "Reasons") and further indicates what type of remedial actions should be taken to correct the situation (in the row labeled "Action"). As shown in the comments section beneath the "Actions" row, a user can select options for automating remedial efforts (using the remediation component 156) in response to the platform detecting that a compliance task is unsatisfactory. This is important given that the timeframe imposed by applicable regulations or laws for taking such remedial efforts can be very short and failure to correct the issue within the timeframe may result in large fines. In this example, the task which was deemed unsatisfactory related to laboratory results indicating the presence of legionella or other harmful biological substances. Thus, the automated remedial efforts can involve automatically transmitting a request to a water treatment specialist to administer biocides to treat the contaminated water and/or automatically transmitting signals to remediation equipment 126 at the site 120 to administer the biocide and control functionality of the remediation equipment 126. Other appropriate remedial actions can be taken in connection with other types of tasks that are deemed to be insufficient or failures.

(d) Schedule Status: The fourth column in the table of FIG. 3A will display an indicator in a row of a site 120 in the event that a service provider has not confirmed the scheduling of a compliance task and/or has not confirmed completion of the task within an expected timeframe. The user selects the indicator to access an interface that provides additional information regarding scheduling information for the site 120.

FIG. 3G illustrates an exemplary scheduling interface 300G that is displayed in response to a user selecting an indicator in the fourth column of FIG. 3A. The interface displays a table of events which correspond to the compliance tasks in FIG. 3E. For each event, the table identifies a task type, an estimated date and time of a service provider's arrival, and the service provider expected to handle the task. The table further includes a status column which indicates whether the associated service provider has confirmed the scheduling of the task and/or completion of the task within an expected timeframe. A user may select an event in the table to obtain additional details about the performance of the event.

FIG. 3H illustrates an exemplary interface 300H that is displayed in response to selecting an event that has not been confirmed by a service provider. Similar to the process details interface described above, an automation feature provides assistance with scheduling a service provider. In certain embodiments, the user preselects or predefines one or more service providers for performing certain tasks and specifies whether the user or the platform provider is to be responsible for sourcing and scheduling the service providers. In certain embodiments, the interface also includes selectable options for activating and deactivating the automation, and for updating or editing the selected service providers. The platform can automatically transmit requests to schedule the selected service providers. The automated scheduling feature can be configured to repeatedly attempt to schedule one or more of the service providers until a confirmation is received from one of the service providers.

(e) Sourcing Status: The fifth column in the table of FIG. 3A will display an indicator in a row of a site 120 in the event that contact information is not provided for any prospective service providers to perform a compliance task. The indicator notifies the user that at least one prospective service provider should be identified to perform each compliance task and that such information has not been provided. The user selects the indicator to access an interface that enables the user to view, add, delete and edit information for prospective service providers.

FIG. 3I illustrates an exemplary sourcing interface 300I that is displayed in response to a user selecting an indicator in the fifth column of FIG. 3A. The interface displays a table that includes a listing of tasks. For each task, the table identifies the task type, the date and time, the team who is responsible for sourcing the service provider (e.g., indicating whether the property manager or the platform provider is responsible for identifying and/or scheduling the service provider), and the number of prospective service providers for handling the task.

If contact information is not provided for any prospective service provider, then an "X" appears in the prospects column. The user may select an entry in either table to view scheduled service providers, to add, remove or edit prospective service providers, and/or to schedule service providers.

FIG. 3J illustrates an exemplary interface 300J that is displayed in response to selecting an entry that includes a listing of prospective service providers from the table displayed in FIG. 3I. The interface includes a table that provides a listing of prospective service providers for handling the selected task for the site 120. The table indicates the service provider's name, contact information (e.g., phone number), distance from the site 120 and history information (e.g., indicating whether the service provider has been utilized to service the site 120 in the past). The user can utilize this information to select or edit a service provider assigned to the task, and/or to add, remove or edit information pertaining to the listed service providers. In certain embodiments, the interface of FIG. 3J may include a selectable option for transmitting a request for services to a service provider and/or a selectable crowd sourcing option for transmitting requests for services to a plurality of service providers.

FIG. 3K illustrates an exemplary interface 300K that is displayed in response to selecting an entry that does not include a listing of prospective service providers from the table displayed in FIG. 3I. A user accesses this interface to add a service provider and to select added service providers for performing tasks.

(f) Compliance Status: This sixth column in the table of FIG. 3A will display an indicator in a row of a site 120 in the event that the site 120 is believed to be or will be in violation of one more regulations, codes or laws. The numerical digit associated with the indicator represents the number of suspected violations. A user selects the indicator to view details on the suspected violations.

FIG. 3L illustrates an exemplary compliance interface 300L that is displayed in response to a user selecting an indicator in the sixth column of FIG. 3A. The interface displays a table that includes a listing of potential violations that may apply to the associated site 120. The interface includes a table that identifies applicable legal standards (e.g., statutes or regulations), estimated ranges of applicable fines, and a description of the violation and/or legal standard. A user selects an entry in the listing of potential violations to find out additional details.

FIG. 3M illustrates an exemplary interface 300M that is displayed in response to selecting an entry in the listing in FIG. 3L. In addition to displaying information pertaining to the fines and description of the potential violation, the interface displays remedy information which explains how to cure the violation. Similar to the process and scheduling interfaces described in above, the automated compliance feature can be configured to automatically engage in remedial efforts in response to the system detecting a violation. This may involve scheduling appropriate service providers to handle remedial tasks and/or performing any other functions to avoid or cure a violation.

(g) Scores: This column displays a score for each property or site 120. The data analyzer and prediction component of the platform may analyze various metrics to determine scores for properties. In this example, the score assigned to a property is with a specified range (e.g., 1-10) and indicates an overall performance measure for complying with applicable regulations. Lower scores indicate poorer compliance, while higher scores indicate greater compliance. A property having a large number of indicators next to a property and greater values for the indicators will have a lower score, while a property having fewer indicators and lower values for the indicators will have greater scores.

As explained above, indicators are added in different columns for various reasons (e.g., failing to provide contact information for contacts, obtaining unsatisfactory process results, failing to schedule service providers, failing to provide prospects for service providers and/or detecting violations). A score assigned to a property may be negatively affected each time an indicator is added to a column associated with the property. As also explained above, property managers can eliminate indicators in various ways (e.g., by supplying missing contact information, taking remedial actions to cure unsatisfactory process results, scheduling service providers, providing information for prospect service providers and/or curing violations). A score assigned to a property may be positively affected each time an indicator is removed from a column associated with the property.

FIG. 3N illustrates an exemplary interface 300N that is displayed in response to a user selecting a score in the seven column of FIG. 3A. The interface displays a bar graph and a line graph that visually illustrates a comparison of the score assigned to the selected site 120 with an average score for the industry (e.g., which may represent any other properties that are subject to the applicable regulations) in terms of compliance. The data analyzer and prediction component may be configured to analyze the aggregated data on the platform to generate these and other graphs.

It should be recognized that while the exemplary interfaces (FIGS. 3A-3N) described relate to interfaces that may be utilized to provide compliance assistance with regulations pertaining to water or cooling towers, similar interfaces may be utilized to provide assistance complying with other types of regulations (e.g., any other environmental or governmental regulations) and/or to provide assistance in connection with other services for the sites (e.g., facility management and maintenance services, plumbing services, electrical services, etc.).

Figure 4:
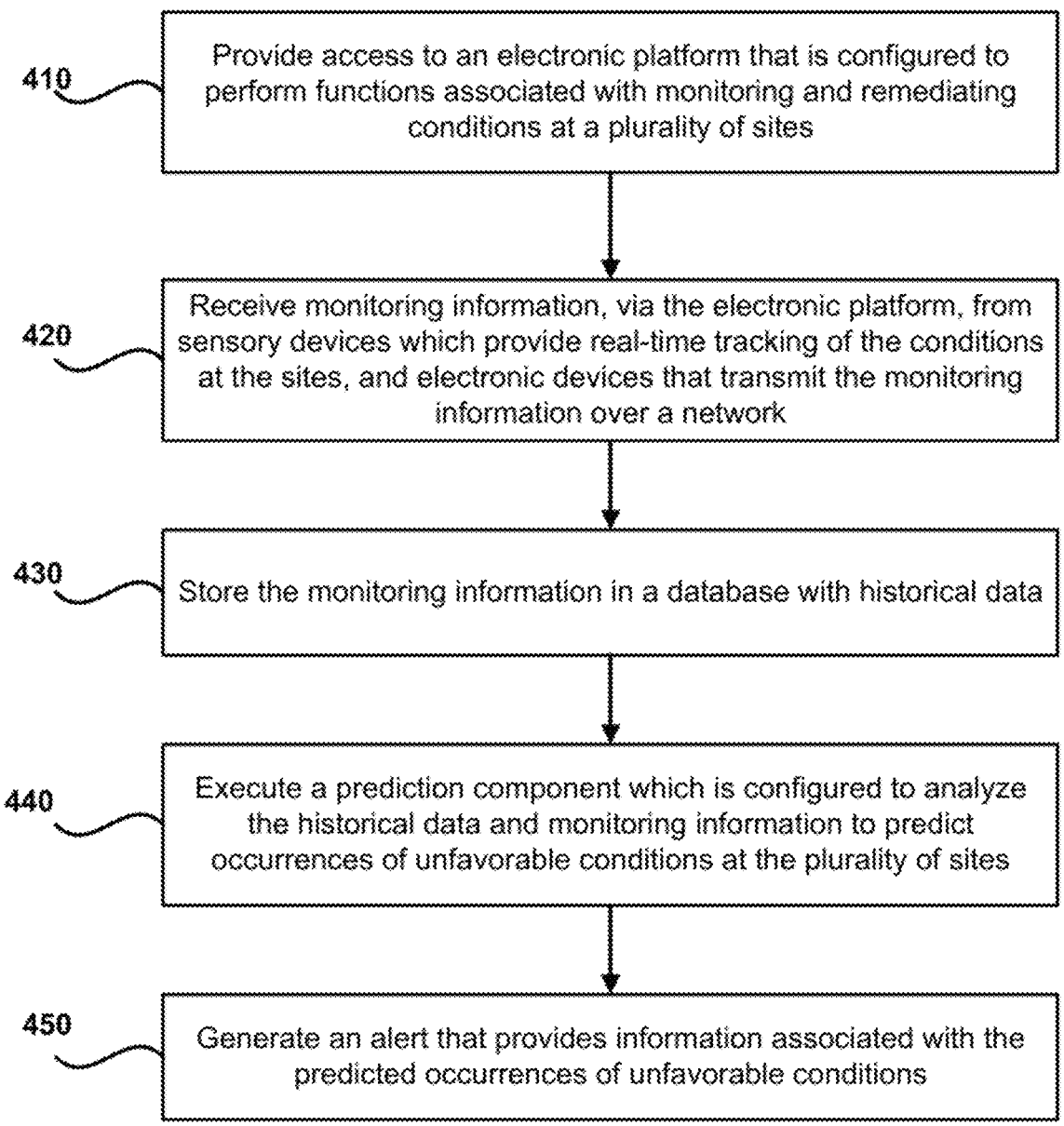
FIG. 4 is a flow chart illustrating an exemplary method for operating a communications and monitoring platform in accordance with certain embodiments.

FIG. 4 is a flow chart illustrating an exemplary method 400 for operating a communications and monitoring 150 in accordance with certain embodiments.

In step 410, access is provided to an electronic communications and monitoring platform 150 that is configured to perform functions associated with monitoring and remediating conditions at a plurality of sites. The electronic platform 150 can be provided on a platform hosting device 130 that is accessible over a network 190 and/or can be stored locally on a user device 110. The electronic platform 150 can be configured to perform functions associated with monitoring and remediating environmental conditions, facilities management conditions, and other conditions at sites 120.

In step 420, monitoring information 250 is received, via the electronic platform 150, from sensory devices 128 which provide real-time tracking of the conditions at the sites 120, and electronic devices that transmit the monitoring information 250 over a network. The sensory devices 128 can be incorporated into, or associated with, the monitoring equipment 124 at the sites. The monitoring equipment 124 can include equipment for monitoring environmental conditions (e.g., monitoring legionella conditions) and facilities management conditions (e.g., monitoring functionality of appliances or devices). The electronic devices include user devices 110 operated by service providers who have accounts with the platform 150.

In step 430, the monitoring information 250 is stored in a database 154 with historical data 240. The historical data 240 includes previously received monitoring information 250 that was recorded and aggregated by the platform 150. The historical information 240 includes additional granular data points, which can include data about any previously occurring events, conditions at sites, weather conditions, equipment specifications/conditions, etc.

In step 440, a prediction component (e.g., data analyzer and predication component 155) is executed which is configured to analyze the historical data 340 and monitoring information 150 to predict occurrences of unfavorable conditions at the plurality of sites 120. For example, in the context of monitoring environmental conditions, this can include predicting occurrences of biological hazards by identifying patterns in the historical data which indicate correlations between elevated levels of biological agents (e.g., legionella) and at least one additional attribute in the historical data 240 (e.g., service providers correlated to elevated levels of legionella or other hazardous conditions, adherence/compliance with regulatory scheme information correlated to elevated levels of legionella or other hazardous conditions, geographic patterns correlated to elevated levels of legionella or other hazardous conditions, and/or weather patterns correlated to elevated levels of legionella or other hazardous conditions). This can also include predicting occurrences of chemical hazards or substances (e.g., asbestos, lead, radon, etc.) by identifying patterns in the historical data which indicate correlations between elevated levels of the chemical hazards or substances and at least one additional attribute in the historical data 240 (e.g., include those attributes listed above for biological hazards). In the context of monitoring facilities management conditions, this can include predicting occurrences of maintenance issues or device failures by identifying patterns in the historical data 240 which indicate correlations between increased instances of these unfavorable conditions and at least one additional attribute in the historical data (e.g., age of the devices or weather patterns).

In step 450, an alert is generated that provides information associated with the predicted occurrences of unfavorable conditions. The alert can be transmitted over the network 190 to one or more electronic user devices 110 to notify property managers of potentially hazardous or unfavorable conditions that are likely to occur at the sites 120. The alerts can include recommendations for preventing the occurrences of the predicted unfavorable conditions and options for scheduling service providers to treat or prevent the predicted hazardous legionella conditions (e.g., for activating remediation equipment 126 and/or scheduling service providers).

While there have been shown, described and pointed out various novel features of the invention as applied to particular embodiments thereof, it should be understood that various omissions, substitutions and changes in the form and details of the systems and methods described may be made by those skilled in the art without departing from the spirit of the invention. Amongst other things, the steps in the methods may be carried out in different orders in cases where such may be appropriate. Those skilled in the art will recognize that the particular hardware and devices that are part of the system described herein, and the general functionality provided by and incorporated therein, may vary in different embodiments of the invention. Accordingly, the particular system components are provided for illustrative purposes and to facilitate a full and complete understanding and appreciation of the various aspects and functionality of particular embodiments of the invention as realized in the system and method embodiments thereof. Those skilled in the art will appreciate that the invention can be practiced in ways other than the described embodiments, which are presented for purposes of illustration and not limitation.

What is claimed is:

1. A system for predicting or detecting hazardous biological conditions, comprising:
   (a) a plurality of cooling or water tower structures located at a plurality of sites;
   (b) a database that stores historical data associated with monitoring legionella conditions at the plurality of sites, the historical data at least including information associated with tracking the legionella conditions in the cooling or water tower structures, prior occurrences of the legionella conditions in the cooling or water tower structures, and attributes associated with the cooling or water tower structures when the prior occurrences of the legionella conditions were detected; and (c) at least one computing device having at least one processor and at least one physical storage device that stores instructions, wherein execution of the instructions by the at least one processor causes the at least one computing device to:
provide an electronic platform that is configured to perform functions associated with monitoring and remediating legionella conditions at the plurality of sites;
receive, via the electronic platform, monitoring information from one or more of: sensory devices which provide real-time tracking of the legionella conditions at the sites, and electronic devices that transmit the monitoring information over a network to track the legionella conditions at the plurality sites;
store the monitoring information in the database with the historical data;
execute a prediction component which is configured to analyze the historical data and monitoring information to predict future occurrences of legionella conditions at one or more of the sites, wherein analyzing the historical data and monitoring information to predict future occurrences of legionella conditions at one or more of the sites includes:
analyzing the historical data to identify correlations between elevated levels of legionella conditions at the cooling or water tower structures when the prior occurrences of the legionella conditions were detected and the attributes at the cooling or water tower structures when the prior occurrences of the legionella conditions were detected; and
predicting the future occurrences of legionella conditions at one or more of the sites based, at least in part, on the identified correlations; and
generate an alert that provides information associated with the predicted future occurrences of legionella conditions.

2. The system of claim 1, wherein the identified correlations include one or more of:
service providers correlated to elevated levels of legionella or other hazardous conditions;
adherence information correlated to elevated levels of legionella or other hazardous conditions;
geographic patterns correlated to elevated levels of legionella or other hazardous conditions; and
weather patterns correlated to elevated levels of legionella or other hazardous conditions.

3. The system of claim 1, wherein the electronic devices are operated by service providers tasked with monitoring or attending to treatment of the legionella conditions at the plurality of sites.

4. The system of claim 1, wherein the electronic platform is configured to transmit alerts to at least one of the sites identifying one or more of the predicted future occurrences of legionella conditions.

5. The system of claim 4, wherein the alerts include:
recommendations for preventing the predicted future occurrences of legionella conditions; and
options for scheduling service providers to treat or prevent the predicted future occurrences of legionella conditions.

6. The system of claim 1, further comprising:
remediation equipment located at the plurality of sites, wherein the remediation equipment is configured to cure or prevent occurrences of legionella conditions.

7. The system of claim 6, wherein the electronic platform is configured to transmit control signals to the remediation equipment over the network for activating and deactivating the remediation equipment.

8. A method for predicting or detecting hazardous biological conditions, comprising:
providing access to a database stored on a non-transitory storage device, the database including historical data associated with monitoring legionella conditions at a plurality of sites, the historical data at least including information associated with tracking the legionella conditions in cooling or water tower structures at the plurality of sites, prior occurrences of the legionella conditions in the cooling or water tower structures, and attributes associated with the cooling or water tower structures when the prior occurrences of the legionella conditions were detected;
providing access to an electronic platform that is configured to perform functions associated with monitoring and remediating legionella conditions at the plurality of sites;
receiving monitoring information, via the electronic platform, from one or more of: sensory devices which provide real-time tracking of the legionella conditions at the sites, and electronic devices that transmit the monitoring information over a network to track the legionella conditions at the plurality sites;
storing the monitoring information in the database with the historical data;
executing a prediction component which is configured to analyze the historical data and monitoring information to predict future occurrences of hazardous legionella conditions at one or more of the sites, wherein analyzing the historical data and monitoring information to predict future occurrences of legionella conditions at one or more of the sites includes:
analyzing the historical data to identify correlations between elevated levels of legionella conditions at the cooling or water tower structures when the prior occurrences of the legionella conditions were detected and the attributes at the cooling or water tower structures when the prior occurrences of the legionella conditions were detected; and
predicting the future occurrences of legionella conditions at one or more of the sites based, at least in part, on the identified correlations; and
generating an alert that provides information associated with the predicted future occurrences of the predicted future occurrences of legionella conditions.

9. The method of claim 8, wherein the identified correlations include one or more of:
service providers correlated to elevated levels of legionella or other hazardous conditions;
adherence information correlated to elevated levels of legionella or other hazardous conditions;
geographic patterns correlated to elevated levels of legionella or other hazardous conditions; and
weather patterns correlated to elevated levels of legionella or other hazardous conditions.

10. The method of claim 8, wherein the electronic devices are operated by service providers tasked with monitoring or attending to treatment of the legionella conditions at the plurality of sites.

11. The method of claim 8, wherein the electronic platform is configured to transmit alerts to at least one of the sites identifying one or more of the predicted future occurrences of legionella conditions.

12. The method of claim 11, wherein the alerts include:
recommendations for preventing the predicted future occurrences of legionella conditions; and
options for scheduling service providers to treat or prevent the predicted future occurrences of legionella conditions.

13. The method of claim 8, further comprising:
using the remediation equipment located at the plurality of sites to cure or prevent occurrences of legionella conditions.

14. The method of claim 13, wherein the electronic platform is configured to transmit control signals to the remediation equipment over the network for activating and deactivating the remediation equipment.

15. A server for predicting or detecting biological, chemical or other hazardous conditions, comprising:
at least one computing device having at least one processor and at least one physical storage device that stores instructions, wherein execution of the instructions by the at least one processor causes the at least one computing device to:
provide access to a database that includes historical data associated with monitoring legionella conditions at a plurality of sites, prior occurrences of the legionella conditions at the sites, and attributes associated with the sites when the prior occurrences of the legionella conditions were detected;
provide access to an electronic platform that is configured to perform functions associated with monitoring and remediating legionella conditions at the plurality of sites;
receive monitoring information, via the electronic platform, from one or more of: sensory devices which provide real-time tracking of the legionella conditions at the sites, and electronic devices that transmit the monitoring information over a network to track the legionella conditions at the plurality sites;
store the monitoring information in the database;
execute a prediction component which is configured to analyze the historical data and monitoring information to predict future occurrences of legionella conditions at the plurality of sites, wherein analyzing the historical data and monitoring information to predict future occurrences of legionella conditions at one or more of the sites includes:
analyzing the historical data to identify correlations between elevated levels of legionella conditions at the sites when the prior occurrences of the legionella conditions were detected and the attributes at the sites when the prior occurrences of the legionella conditions were detected; and
predicting the future occurrences of legionella conditions at one or more of the sites based, at least in part, on the identified correlations; and
generate an alert that provides information associated with the predicted future occurrences of legionella conditions.

16. The server of claim 15, wherein the electronic platform is configured to transmit alerts to at least one of the sites identifying one or more of the predicted future occurrences of legionella conditions.

17. The server of claim 16, wherein the alerts include:
recommendations for preventing the predicted future occurrences of legionella conditions; and
options for scheduling service providers to treat or prevent the predicted future occurrences of legionella conditions.

18. The system of claim 1, wherein:
the monitoring information indicates current statuses of the plurality of sites;
the current statuses of the plurality of sites is utilized to predict the future occurrences of legionella conditions at one or more of the sites based, at least in part, on the identified correlations.

19. The system of claim 1, wherein:
the attributes associated with the cooling or water tower structures when the prior occurrences of the legionella conditions were detected indicate weather conditions that were present during the prior occurrences of the legionella conditions; and
the identified correlations used to predict the future occurrences of legionella conditions are based, at least in part, on one or more detected weather patterns that are correlated with elevated levels of legionella conditions at the cooling or water tower structures.

20. The system of claim 1, wherein:
the attributes associated with the cooling or water tower structures when the prior occurrences of the legionella conditions were detected identify equipment that was present during the prior occurrences of the legionella conditions; and
the identified correlations used to predict the future occurrences of legionella conditions are based, at least in part, on equipment that is correlated with elevated levels of legionella conditions at the cooling or water tower structures.

21. The system of claim 1, wherein:
the attributes associated with the cooling or water tower structures when the prior occurrences of the legionella conditions were detected identify service providers who serviced the cooling or water tower structures associated with the prior occurrences of the legionella conditions; and
the identified correlations used to predict the future occurrences of legionella conditions are based, at least in part, on one or more service providers correlated with elevated levels of legionella conditions at the cooling or water tower structures.

* * * * *